United States Patent
Eckert et al.

(10) Patent No.: US 12,094,614 B2
(45) Date of Patent: Sep. 17, 2024

(54) RADAR APPARATUS WITH NATURAL CONVECTION

(71) Applicant: Koko Home, Inc., Palo Alto, CA (US)

(72) Inventors: Bradley Michael Eckert, Palo Alto, CA (US); Luca Rigazio, Los Gatos, CA (US); Neal Khosla, Palo Alto, CA (US); Kiran Joshi, Palo Alto, CA (US); Vinod Khosla, Menlo Park, CA (US)

(73) Assignee: Koko Home, Inc., Los Angeles, CA (US)

( * ) Notice: Subject to any disclaimer, the term of this patent is extended or adjusted under 35 U.S.C. 154(b) by 0 days.

(21) Appl. No.: 18/214,246

(22) Filed: Jun. 26, 2023

(65) Prior Publication Data

US 2023/0335292 A1     Oct. 19, 2023

Related U.S. Application Data

(63) Continuation-in-part of application No. 17/883,654, filed on Aug. 9, 2022, which is a continuation of (Continued)

(51) Int. Cl.
*G16H 50/30*     (2018.01)
*A61B 5/00*     (2006.01)
(Continued)

(52) U.S. Cl.
CPC ........... *G16H 50/30* (2018.01); *A61B 5/0015* (2013.01); *A61B 5/0205* (2013.01);
(Continued)

(58) Field of Classification Search
CPC .... G16H 50/30; A61B 5/0015; A61B 5/0205; A61B 5/7221; A61B 5/746;
(Continued)

(56) References Cited

U.S. PATENT DOCUMENTS 7,436,348 B2    10/2008 Nohmi
7,654,948 B2     2/2010 Kaplan et al.
(Continued)

FOREIGN PATENT DOCUMENTS

CN    207869389 U    9/2018
EP        2952927    12/2015
(Continued)

OTHER PUBLICATIONS

"International Application Serial No. PCT/US2019/062043, International Preliminary Report on Patentability dated May 27, 2021", 7 pgs.
(Continued)

*Primary Examiner* — Andrew W Bee
(74) *Attorney, Agent, or Firm* — Schwegman Lundberg & Woessner, P.A.

(57) ABSTRACT

An apparatus detects and measures vital signs of each human target by a continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans are living in a home. The apparatus has a natural convection spatial flow path that draws heat from at least one processor, one fan-less radar and a heat sink.

20 Claims, 18 Drawing Sheets

Related U.S. Application Data application No. 17/526,283, filed on Nov. 15, 2021, now Pat. No. 11,462,330, which is a continuation of application No. 17/244,554, filed on Apr. 29, 2021, now abandoned, and a continuation-in-part of application No. 16/840,085, filed on Apr. 3, 2020, said application No. 17/244,554 is a continuation of application No. 16/103,829, filed on Aug. 14, 2018, now Pat. No. 11,004,567.

(60) Provisional application No. 62/545,921, filed on Aug. 15, 2017.

(51) Int. Cl.
A61B 5/0205 (2006.01)
G06N 5/025 (2023.01)
A61B 5/024 (2006.01)
A61B 5/08 (2006.01)
A61B 5/11 (2006.01)
G16H 40/60 (2018.01)
H04B 1/04 (2006.01)
H04B 1/16 (2006.01)

(52) U.S. Cl.
CPC ............ A61B 5/7221 (2013.01); G06N 5/025 (2013.01); A61B 5/024 (2013.01); A61B 5/0816 (2013.01); A61B 5/1113 (2013.01); A61B 5/1118 (2013.01); A61B 5/741 (2013.01); A61B 5/746 (2013.01); A61B 2503/08 (2013.01); A61B 2505/07 (2013.01); A61B 2560/0242 (2013.01); A61B 2562/0204 (2013.01); A61B 2562/0219 (2013.01); A61B 2562/0223 (2013.01); A61B 2562/0228 (2013.01); A61B 2562/0271 (2013.01); A61B 2562/028 (2013.01); A61B 2562/029 (2013.01); G16H 40/60 (2018.01); H04B 1/04 (2013.01); H04B 1/16 (2013.01)

(58) Field of Classification Search
CPC .... A61B 2560/0242; A61B 2562/0219; A61B 2562/0223; G06N 5/025
See application file for complete search history.

(56) References Cited

U.S. PATENT DOCUMENTS

| | | |
|---|---|---|
| 7,916,066 B1 | 3/2011 | Osterweil |
| 7,925,995 B2 | 4/2011 | Krumm et al. |
| 8,446,253 B2 | 5/2013 | Ramchandran et al. |
| 8,512,221 B2 | 8/2013 | Kaplan et al. |
| 8,562,526 B2 | 10/2013 | Heneghan et al. |
| 8,606,249 B1 | 12/2013 | Goodwin |
| 9,196,257 B2 | 11/2015 | Schultz-Amling et al. |
| 9,309,782 B2 | 4/2016 | Kareff et al. |
| 9,311,802 B1 | 4/2016 | Chin et al. |
| 9,319,782 B1 | 4/2016 | Crump et al. |
| 9,807,725 B1 | 10/2017 | Vitus et al. |
| 9,972,917 B2 | 5/2018 | Vacanti et al. |
| 10,008,886 B2 | 6/2018 | Leabman |
| 10,222,474 B1 | 3/2019 | Raring et al. |
| 10,271,019 B1 | 4/2019 | Berg et al. |
| 10,345,874 B1 | 7/2019 | Narasimhan et al. |
| 10,457,161 B2 | 10/2019 | Lu-Dac et al. |
| 10,568,565 B1 | 2/2020 | Kahn et al. |
| 10,574,945 B1 | 2/2020 | Seyfi et al. |
| 10,623,897 B1 | 4/2020 | Wu et al. |
| 10,928,498 B1 | 2/2021 | Li et al. |
| 10,936,880 B2 | 3/2021 | Eronen et al. |
| 11,043,038 B1 | 6/2021 | Ngai et al. |
| 11,105,912 B2 | 8/2021 | Yokev et al. |
| 11,719,804 B2 | 8/2023 | Rigazio et al. |
| 11,736,901 B2 | 8/2023 | Rigazio et al. |
| 2005/0007269 A1 | 1/2005 | Carrara et al. |
| 2005/0154929 A1 | 7/2005 | Ahrens et al. |
| 2006/0053110 A1 | 3/2006 | McDonald et al. |
| 2006/0152404 A1 | 7/2006 | Fullerton et al. |
| 2006/0284791 A1 | 12/2006 | Chen et al. |
| 2006/0291473 A1 | 12/2006 | Chase et al. |
| 2007/0205937 A1 | 9/2007 | Thompson et al. |
| 2007/0297695 A1 | 12/2007 | Aratani et al. |
| 2009/0167862 A1 | 7/2009 | Jentoft |
| 2009/0203972 A1 | 8/2009 | Heneghan et al. |
| 2009/0224963 A1 | 9/2009 | Nakanishi |
| 2009/0264715 A1 | 10/2009 | Auphan |
| 2010/0026479 A1 | 2/2010 | Tran |
| 2010/0048256 A1 | 2/2010 | Huppi |
| 2010/0141506 A1 | 6/2010 | Gulden et al. |
| 2010/0152600 A1 | 6/2010 | Droitcour et al. |
| 2010/0321229 A1 | 12/2010 | Dwelly et al. |
| 2011/0077758 A1 | 3/2011 | Tran |
| 2011/0187816 A1 | 8/2011 | Shimizu |
| 2011/0190594 A1 | 8/2011 | Heit et al. |
| 2011/0199254 A1 | 8/2011 | Bishop et al. |
| 2011/0242305 A1 | 10/2011 | Peterson et al. |
| 2012/0044355 A1 | 2/2012 | Jamtgaard et al. |
| 2012/0062729 A1 | 3/2012 | Hart et al. |
| 2012/0065944 A1 | 3/2012 | Nielsen et al. |
| 2012/0161968 A1 | 6/2012 | Bodapati et al. |
| 2012/0275236 A1 | 11/2012 | Hess |
| 2013/0053653 A1 | 2/2013 | Cuddihy et al. |
| 2013/0207831 A1 | 8/2013 | Fullerton |
| 2013/0278416 A1 | 10/2013 | Button et al. |
| 2014/0022940 A1 | 1/2014 | Apte et al. |
| 2014/0155705 A1 | 6/2014 | Papadopoulos et al. |
| 2014/0168507 A1 | 6/2014 | Renaud |
| 2014/0207292 A1 | 7/2014 | Ramagem et al. |
| 2014/0316261 A1 | 10/2014 | Lux et al. |
| 2014/0335893 A1 | 11/2014 | Ronen |
| 2014/0375521 A1 | 12/2014 | Andujar et al. |
| 2015/0022349 A1 | 1/2015 | Smith et al. |
| 2015/0079809 A1 | 3/2015 | Silva et al. |
| 2015/0182162 A1 | 7/2015 | Zhao |
| 2015/0233598 A1 | 8/2015 | Shikii et al. |
| 2015/0238137 A1 | 8/2015 | Eyal et al. |
| 2015/0245167 A1 | 8/2015 | Bobrow et al. |
| 2015/0265922 A1 | 9/2015 | Yamane et al. |
| 2015/0286948 A1 | 10/2015 | Luca et al. |
| 2015/0301167 A1 | 10/2015 | Sentelle |
| 2015/0302323 A1 | 10/2015 | Connolly |
| 2015/0310726 A1 | 10/2015 | Sager et al. |
| 2016/0055332 A1 | 2/2016 | Jeansonne et al. |
| 2016/0151603 A1 | 6/2016 | Shouldice et al. |
| 2016/0249021 A1 | 8/2016 | McAleenan et al. |
| 2016/0270205 A1 | 9/2016 | Kamimura |
| 2016/0337441 A1 | 11/2016 | Bloomquist et al. |
| 2016/0360362 A1 | 12/2016 | Do et al. |
| 2016/0377705 A1 | 12/2016 | Zack et al. |
| 2017/0005958 A1 | 1/2017 | Frenkel et al. |
| 2017/0038456 A1 | 2/2017 | Smith |
| 2017/0039517 A1 | 2/2017 | Amann et al. |
| 2017/0086202 A1 | 3/2017 | Chen |
| 2017/0108581 A1 | 4/2017 | Morley |
| 2017/0328995 A1 | 11/2017 | Marschalkowski et al. |
| 2018/0012080 A1 | 1/2018 | Glaser et al. |
| 2018/0031374 A1 | 2/2018 | Hepler et al. |
| 2018/0043247 A1 | 2/2018 | Vandonkelaar |
| 2018/0050800 A1 | 2/2018 | Boykin et al. |
| 2018/0064388 A1 | 3/2018 | Heneghan et al. |
| 2018/0116606 A1 | 5/2018 | Li et al. |
| 2018/0143320 A1 | 5/2018 | Steever et al. |
| 2018/0153058 A1 | 5/2018 | Hirai et al. |
| 2018/0167140 A1 | 6/2018 | Brandt-pearce et al. |
| 2018/0204470 A1 | 7/2018 | Rezvani et al. |
| 2018/0245927 A1 | 8/2018 | Frish et al. |
| 2018/0295535 A1 | 10/2018 | Kavars et al. |
| 2018/0351775 A1 | 12/2018 | Zhang et al. |
| 2018/0357871 A1 | 12/2018 | Siminoff |
| 2018/0374143 A1 | 12/2018 | Williamson et al. |
| 2019/0019295 A1 | 1/2019 | Lehtiniemi et al. |
| 2019/0033440 A1 | 1/2019 | Boolos et al. |

(56) References Cited

U.S. PATENT DOCUMENTS

| | | |
|---|---|---|
| 2019/0043466 A1 | 2/2019 | Masterson et al. |
| 2019/0053707 A1 | 2/2019 | Lane et al. |
| 2019/0057777 A1 | 2/2019 | Joshi et al. |
| 2019/0072669 A1 | 3/2019 | Duque et al. |
| 2019/0088098 A1 | 3/2019 | Gangumalla et al. |
| 2019/0108913 A1 | 4/2019 | Coke et al. |
| 2019/0146077 A1 | 5/2019 | Kravets et al. |
| 2019/0158494 A1 | 5/2019 | Nakayama et al. |
| 2019/0159960 A1 | 5/2019 | Nakata et al. |
| 2019/0197866 A1 | 6/2019 | Mukundala et al. |
| 2019/0207650 A1 | 7/2019 | Kearney et al. |
| 2019/0219403 A1 | 7/2019 | Hu |
| 2019/0278555 A1 | 9/2019 | Carvajal et al. |
| 2019/0279479 A1 | 9/2019 | Reunamaki et al. |
| 2019/0289417 A1 | 9/2019 | Tomlin et al. |
| 2019/0302252 A1 | 10/2019 | Santra et al. |
| 2019/0317239 A1 | 10/2019 | Olsson et al. |
| 2019/0347925 A1 | 11/2019 | Faltaous et al. |
| 2019/0372363 A1 | 12/2019 | Cutcher et al. |
| 2019/0375103 A1 | 12/2019 | Cui et al. |
| 2020/0022646 A1 | 1/2020 | Brown |
| 2020/0053574 A1 | 2/2020 | Hasan et al. |
| 2020/0054236 A1 | 2/2020 | Qi et al. |
| 2020/0079363 A1 | 3/2020 | Frederick et al. |
| 2020/0088870 A1 | 3/2020 | Tsiklauri et al. |
| 2020/0097006 A1 | 3/2020 | Liu et al. |
| 2020/0097092 A1 | 3/2020 | Tzadok |
| 2020/0103486 A1 | 4/2020 | Knaappila |
| 2020/0103513 A1 | 4/2020 | Knaappila |
| 2020/0103516 A1 | 4/2020 | Kim et al. |
| 2020/0137884 A1 | 4/2020 | Markish et al. |
| 2020/0143123 A1 | 5/2020 | Shen et al. |
| 2020/0168339 A1 | 5/2020 | Correnti |
| 2020/0196110 A1 | 6/2020 | Jakobsson |
| 2020/0204541 A1 | 6/2020 | Nair et al. |
| 2020/0234030 A1 | 7/2020 | Baheti et al. |
| 2020/0271747 A1 | 8/2020 | Wu et al. |
| 2020/0272268 A1 | 8/2020 | Shin et al. |
| 2020/0310749 A1 | 10/2020 | Miller et al. |
| 2020/0397310 A1 | 12/2020 | Gu et al. |
| 2021/0011121 A1 | 1/2021 | Arbabian et al. |
| 2021/0033724 A1 | 2/2021 | Zhang et al. |
| 2021/0046650 A1 | 2/2021 | Deyle et al. |
| 2021/0063214 A1 | 3/2021 | Li et al. |
| 2021/0065891 A1 | 3/2021 | Li et al. |
| 2021/0150873 A1 | 5/2021 | Shouldice et al. |
| 2021/0194206 A1 | 6/2021 | Raring et al. |
| 2021/0197834 A1 | 7/2021 | Shaker |
| 2021/0233539 A1 | 7/2021 | Wexler et al. |
| 2021/0358637 A1 | 11/2021 | Devdas |
| 2022/0016519 A1 | 1/2022 | Van Der Steen et al. |
| 2022/0051677 A1 | 2/2022 | Park et al. |
| 2022/0075051 A1 | 3/2022 | Woo et al. |
| 2022/0268916 A1* | 8/2022 | Nagpal ................. H04R 1/406 |

FOREIGN PATENT DOCUMENTS

| | | |
|---|---|---|
| GB | 2520169 A | 5/2015 |
| KR | 101536249 B1 | 7/2015 |
| WO | 2007143535 | 12/2007 |
| WO | WO-2016193972 A2 | 12/2016 |

OTHER PUBLICATIONS

"International Application Serial No. PCT/US2019/062043, International Search Report dated Mar. 19, 2020", 3 pgs.
"International Application Serial No. PCT/US2019/062043, Written Opinion dated Mar. 19, 2020", 5 pgs.
"International Application Serial No. PCT/US2022/039857, International Search Report dated Jan. 3, 2023", 3 pgs.
"International Application Serial No. PCT/US2022/039857, Invitation to Pay Additional Fees dated Oct. 20, 2022", 2 pgs.
"International Application Serial No. PCT/US2022/039857, Written Opinion dated Jan. 3, 2023", 5 pgs.
"International Search Report: International Application Serial No. PCT/US2019/062043, International Search Report dated Mar. 19, 2020", 3 pgs.
"International Written Opinion: International Application Serial No. PCT/US2019/062043, Written Opinion dated Jul. 13, 2005", 5 pgs.
Chen, et al., "Google Translation of CN207869389", (Sep. 2018), 5 pgs.
Ganis, "A Portable 3D Imaging FMCW MIMO Radar Demonstrator with a 24x24 Antenna Array for Medium Range Applications", (2018), 15 pgs.
Hannun, Awni, et al., "Sequence-tosequence speech recognition with time-depth separable convolutions", arXiv:1904.02619, (Apr. 2019), 5 pgs.
He, Kaiming, et al., "Deep Residual Learning for Image Recognition", arXiv preprint, arXiv:1512.03385v1 [cs.CV], (Dec. 10, 2015), 12 pgs.
Khan, et al., "A Detailed Algorithm for Vital Sign Monitoring of a Stationary/Non-Stationary Human Through IR-UWB Radar", Sensors 2017, (Feb. 4, 2017), 15 pgs.
Lee, "Design and Performance of a 24-GHz Switch-Antenna Array FMCW Radar System for Automotive Applications", (2010), 8 pgs.
Lien, Jaime, et al., "Soli: Ubiquitous Gesture Sensing with Millimeter Wave Radar", ACM Transactions on Graphics (TOG), vol. 35 Issue 4, Article 142, (Jul. 2016), 19 pgs.
Rahman, Tauhidur, et al., "A Contactless Unobtrusive Sleep Sensing System Using Short-Range Doppler Radar", UBICOMP '15, Osaka, Japan, (Sep. 7-11, 2015), 12 pgs.
Ravanelli, M, et al., "Speech and Speaker Recognition from Raw Waveform with SincNet", arXiv:1812.05920v2, (Feb. 15, 2019), 5 pgs.
Sherman, "AN/FPS-115 Pave Paws Radar", (2000), 4 pgs.
Suzuki, et al., "An Approach to a Non-Contact Vital Sign Monitoring Using Dual-Frequency Microwave Radars for Elderly Care", J. Biomedical Science and Engineering 6, (2013), 704-711.
Tian, Yonglong, "RF-Based Fall Monitoring Using Convolutional Neural Networks", Proc. ACM Interact. Mob. Wearable Ubiquitous Technol., vol. 2, No. 3, Article 137, (Sep. 2018). 24 pgs.
Tokoro, S, et al., "Electronically scanned millimeter-wave radar for pre-crash safety and adaptive cruise control system", In IEEE IV2003 Intelligent Vehicles Symposium, (Jun. 2003), 6 pgs.
Wang, Zhihua, et al., "A Review of Wearable Technologies for Elderly Care that Can Accurately Track Indoor Position, Recognize Physical Activities and Monitor Vital Signs in Real Time", (Feb. 10, 2017), 36 pgs.
Yang, et al., "Vital Sign and Sleep Monitoring Using Millimeter Wave", ACM Transactions on Sensor Networks, vol. 13, No. 2, Artical 14, (Apr. 2017), 32 pgs.
"FCC Equipment Test Report of 10.525 GHz field disturbance sensor in SleepScore Max Bedside Monitor", Compliance Engineering Ireland LTD, (Sep. 20, 2013), 25 pgs.
"International Application Serial No. PCT US2022 039857, International Preliminary Report on Patentability mailed Feb. 22, 2024", 7 pgs.
Cippitelli, E, et al., "Radar and RGB-Depth Sensors for Fall Detection: A Review", in IEEE Sensors Journal, vol. 17, No. 12, (Jun. 15, 2017), 3585-3604.
Li, et al., "Radar Remote Monitoring of Vital Signs", IEEE Microwave Magazine, (Feb. 2009), 47-56.
Li, et al., "Through-Wall Detection of Human Being's Movement by UWB Radar", IEEE GeoScience and Remote Sensing Letters, vol. 9, No. 6, (Nov. 2012), 1079-1083.
Oladimeji, Onalaja, "Advances in UWB-Based Indoor Position Estimation and Its Application in Fall Detection", Ph.D. Degree Thesis, London South Bank University, (Jun. 2015), 190 pgs.

* cited by examiner

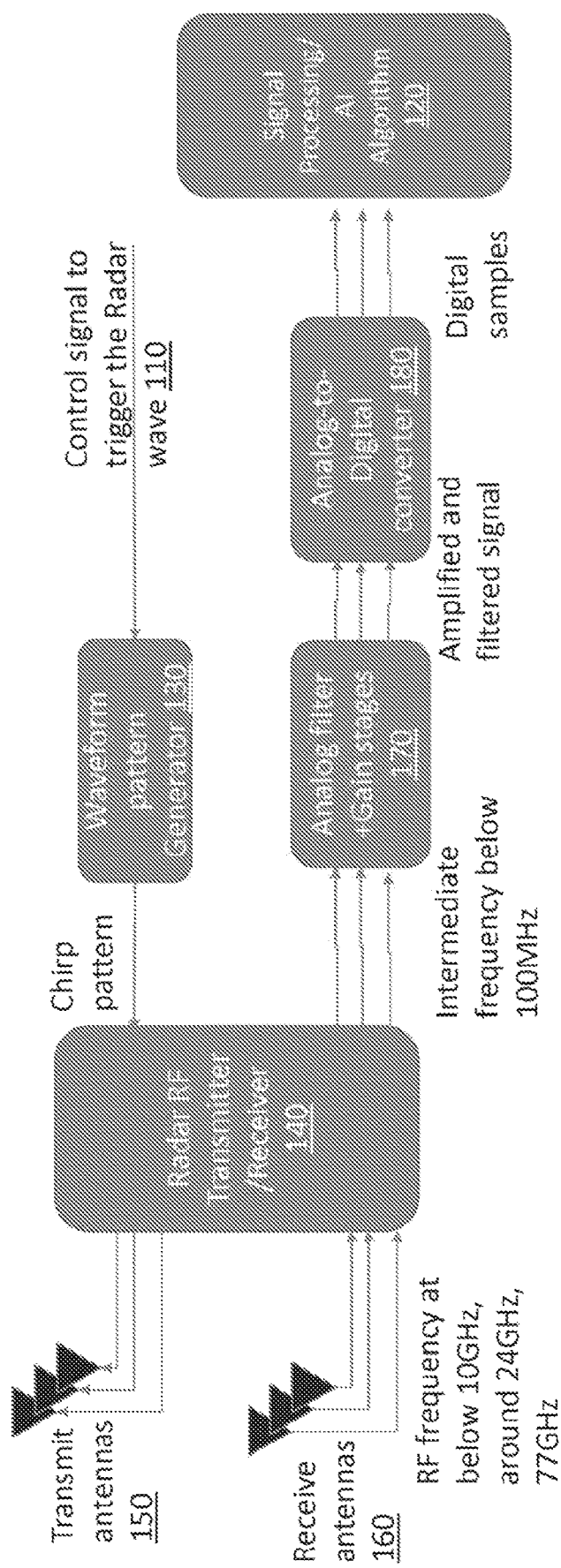

Figure 2: Full Sensor Array 200

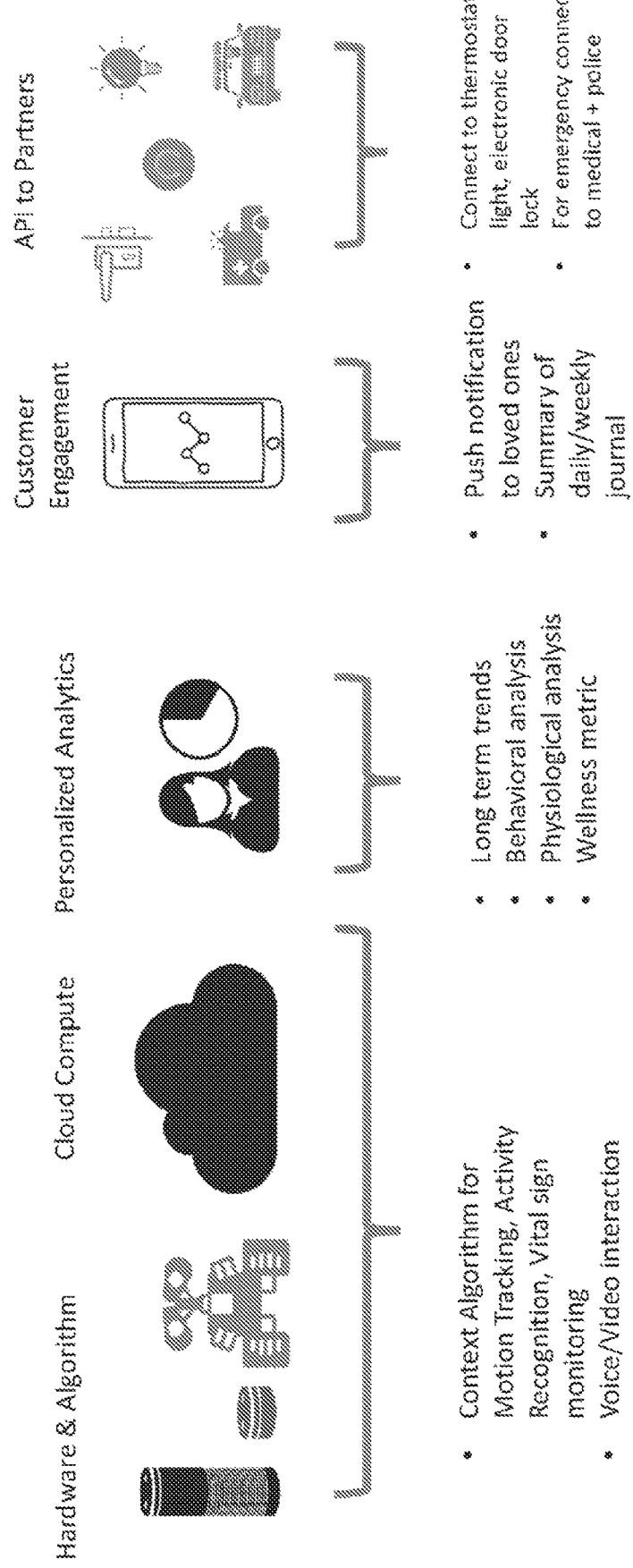

Figure 4  Hardware Units of ADL/Security System

1) Hub
What does it do?
- Activity + vital recognition
- Act as a controller for all other hardware units
- Aggregates sensor data from all units to understand the global context
- Gateway to internet Where? Place it in a central location of house How? Radar, Camera, WiFi receivers, microphone, speaker, pressure, temp, carbon mono, UV

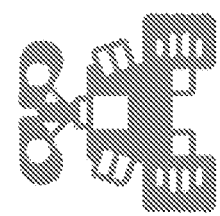

2) Node
What does it do?
- Activity + vital recognition
- Understands the local context and pass that info to Hub Where? Place it near areas where certain critical events are likely to happen

3) Mobile
What does it do?
- Patrolling
- Probe locations where the static units have recognized interesting events Where? it's mobile, will be continuously move around the house How? Radar, Camera, WiFi receivers, microphone, speaker, Inertial (Gyro, Accelerometer, Compass), temp, UWB

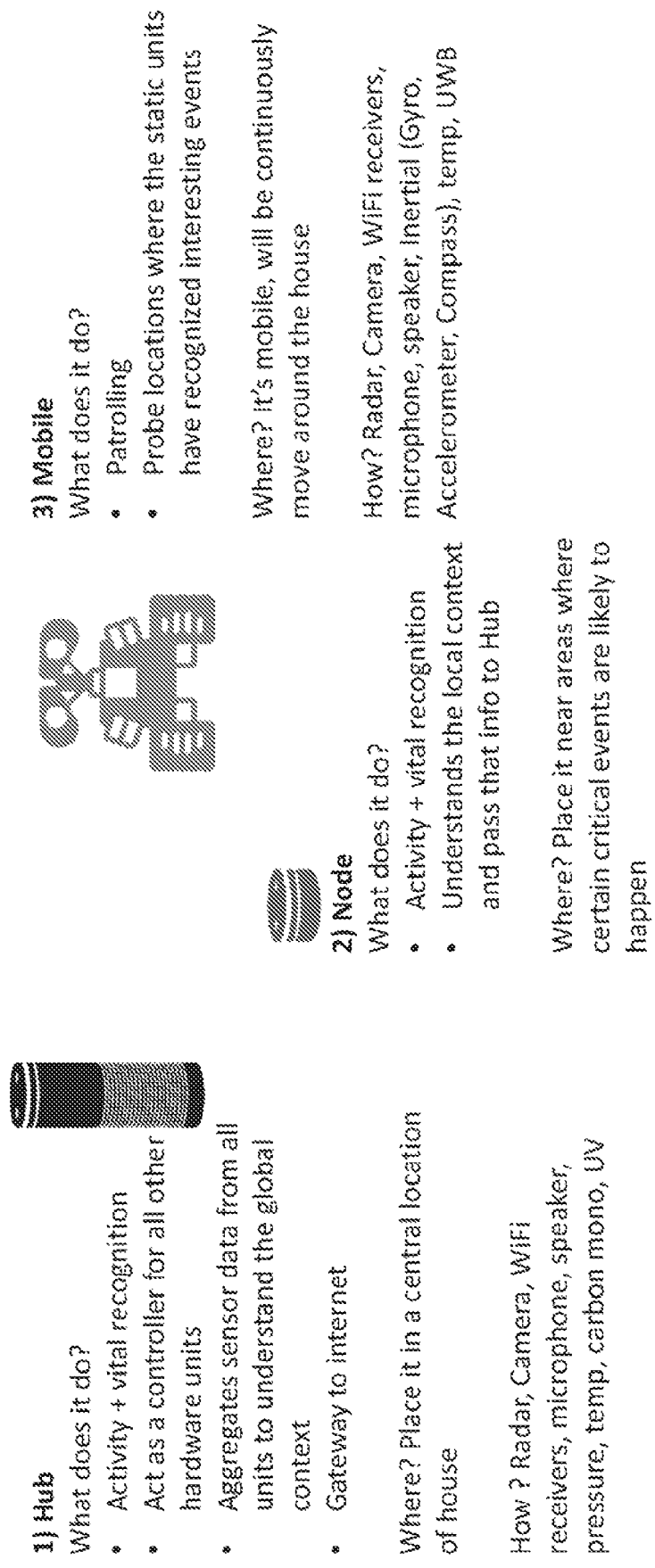

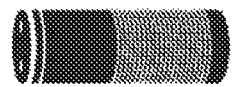
Figure 5: Hub

Figure 7: Mini Node

Figure 9: Mobile Node

Figure 11: Categories of Senior ADL

- Basic ADLs:
  - Bathing
  - Brushing teeth
  - Dressing
  - Using Toilet
  - Eating and Drinking
  - Sleeping
- Instrumented ADLs
  - Preparing meals
  - Preparing drinks
  - Resting
  - Housekeeping
  - Using a telephone
  - Taking medicine
- Ambulatory Activities
  - Walking:
  - Doing Exercise : Running, cycling
  - Transitional Activities : Sit-to-stand, stand-to-sit, lie-to-sit in and out of bed or chair
  - Stationary Activities : sits in sofa, stand for a while, lie in bed or sofa Figure 12: Activities List

- Going Out
- Preparing Breakfast
- Having Breakfast
- Preparing Lunch
- Having Lunch
- Preparing Dinner
- Having Dinner
- Washing Dishes
- Having Snack
- Sleeping
- Watching TV
- Studying
- Having Shower
- Toileting
- Having Nap
- Using Internet
- Reading Book
- Shaving
- Brushing Teeth
- Telephone
- Listening Music
- Doing Cleaning
- Having Conversation
- Entertain Guest

RADAR APPARATUS WITH NATURAL CONVECTION

CROSS-REFERENCE TO RELATED APPLICATION

The present application is a continuation-in-part of U.S. patent application Ser. No. 17/883,654 filed Aug. 9, 2022, which is a continuation of U.S. patent application Ser. No. 17/526,283, filed Nov. 15, 2021, which is a continuation of U.S. patent application Ser. No. 17/244,554, filed Apr. 29, 2021, which is a continuation of U.S. patent application Ser. No. 16/103,829 filed Aug. 14, 2018, now U.S. Pat. No. 11,004,567, which is a non-provisional of, and claims the benefit of priority to, U.S. Prov. Pat. App. No. 62/545,921 filed Aug. 15, 2017, the entire contents of each is incorporated herein by reference.

This application is a continuation-in-part of U.S. patent application Ser. No. 16/840,085 filed Apr. 3, 2020, which is incorporated herein by reference.

TECHNICAL FIELD

The present disclosure relates to techniques, including a method and system, for cooling or controlling heat in a system that processes signals using artificial intelligence (AI) techniques to monitor, detect and act on activities. In an example, the signals can be from both active and passive sensors, among others. Merely by way of examples, various applications can include activities of daily life, and others.

BACKGROUND

Various conventional techniques exist for monitoring people within a home or building environment. Such techniques include use of cameras to view a person. Other techniques include a pendant or other sensing device that is placed on the person to monitor his/her movement; examples include Personal Emergency Response Systems (PERS) devices such as LifeAlert® and Philips® Life-Line—each of which are just panic buttons for seniors to press in case of an emergency. Unfortunately, all of these techniques have limitations. That is, each of these techniques fails to provide a reliable and high-quality signal to accurately detect a fall or other life activity of the person being monitored. Many people often forget to wear the pendant, or a power source for the pendant runs out. Also, elderly people do not want to look like they are old, so often times elderly people do not wear the pendant.

From the above, it is seen that techniques for identifying and monitoring a person are highly desirable while controlling for heat in the system.

Examples also relate to techniques, including a method and system, for processing audio, motion, ultra-wide band ("UWB") and frequency modulated continuous wave ("FMCW") signals using a plurality of antenna array, and other conditions and events. In particular, the inventive subject matter provides an apparatus using a thermal and mechanical confirmation to allow heat-generating multi-core processors and artificial intelligence processes to operate without forced air convection, e.g., without a fan, therefore preventing fan-produced noise and vibration, which can interfere with accuracy required in a radar system. Merely by way of example, various applications can include daily life, and others.

SUMMARY

According to examples, techniques, including a method and system, for processing signals using artificial intelligence techniques to monitor, detect, and act on activities are provided. In an example, the signals can be from both active and passive sensors, among others. Merely by way of examples, various applications can include daily life, and others.

In an example, a sensor array in a single box can be placed in a home or a single box (acting as a base station) that talks to multiple helper sensor boxes can be distributed throughout a living space of the home. In an example, the sensor array communicates with a backend server via standard connectivity solutions, such as Wi-Fi, cellular, or others. In an example, the technique uses distributed processing where processing of the data occurs inside the sensor array and in a cloud server. In an example, artificial intelligence (AI) techniques are included. Depending upon the example, the processed data are disseminated to various interested parties (e.g., the patient/user of the monitor, children of an elderly person, caretakers, Emergency Medical Response team, etc.) via different communication channels, such as smartphone app, SMS, email, voicemail, and other techniques.

In an example, an example of a device provides a method of detecting a status of a human being or target. The method may include transferring, using a wireless transmitter, a wireless signal being selected from one or more of a frequency being less than about 10 G Hz, 24 G Hz, 60 G Hz, or 77 G Hz and greater. The method may include capturing a back-scattered signal, using a radio frequency (RF) antenna, from the wireless signal. The method may include processing the back-scattered signal to extract one or more of a direction, signal strength, distance, and other information over a time period. The method may include extracting, using a signal processing process, vital signs of a human, the vital signs including a heart rate or a respiration rate. The method may include creating a baseline for each of the vital signs. The method may include extracting, using an AI process, a physical activity of the human being. The method may include creating a physical activity baseline for the physical activity and determining a confidence level of each of the received vital signals and each of the physical activities. The method may include transferring an alert to another target upon a triggering even based upon the confidence level of each of the received vital signals and each of the physical activities and correlating each vital sign, using an artificial intelligence process, with one or more patterns or the baseline for each of the vital signs.

In an example, an example of a device provides a system for monitoring and detecting an activity of a human target. The system has a sensor array, the sensor array comprising a plurality of passive sensors. In an example, each of the plurality of passive sensors is spatially disposed in spatial region of a living area. In an example, the system has a wireless backscattering detection system. The wireless backscattering detection system has a control line coupled to a processing device. In an example, the control line is configured with a switch to trigger an initiation of a wireless signal. The detection system has a waveform pattern generator coupled to the control line, an RF transmitter coupled to the waveform pattern generator, a transmitting antenna coupled to the RF transmitter, an RF receiver, an RF receiving antenna coupled to the RF receiver, an analog front end comprising a filter, an analog-to-digital converter coupled to the analog front end, a signal processing device coupled to the analog-to-digital converter, and an artificial intelligence processor coupled to the signal processing device and configured to process information associated with a backscattered signal captured from the RF receiving antenna. Further details of each of these elements can be found throughout the present specification and more particularly below.

The above examples and implementations are not necessarily inclusive or exclusive of each other and may be combined in any manner that is non-conflicting and otherwise possible, whether they be presented in association with a same, or a different, embodiment or example or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above examples implementations are illustrative, rather than limiting.

Further, techniques related to a method and system for processing audio, UWB, FMCW signals using a plurality of antenna array, and other signals and events, are provided. In particular, the inventive subject matter provides an apparatus using a thermal and mechanical confirmation to allow heat-generating multi-core processors and artificial intelligence processes to operate without forced air convection. Merely by way of example, various applications can include daily life, and others.

In an example, the apparatus has a natural convection spatial flow path initiating from the processing device through the plurality of openings, and initiating from the radar through the plurality of apertures, to maintain an interior region of the housing within a temperature range such as 10 degrees Celsius to no greater than 90 degrees C., while being substantially free from an electromagnetic noise, mechanical noise such as vibration that may interfere with the sensors, and a stream of forced convection. In an example, the apparatus has a heat sink region coupled to an upper portion of the housing and configured within a region of the natural convection spatial flow path to maintain the interior region within the temperature range, e.g., 10 degrees C. to no greater than 90 degrees C.

In an example, the present apparatus and related method provides a lower chamber temperature to allow for efficient RF transmission and receiving of RF backscattered signals, rather than a higher chamber temperature generated by power-consuming processing devices, such as micro-processors, digital signal processors, artificial intelligence processors, alone or in combination with other devices. In an example, the apparatus is fan free, that is, has no fan or mechanical device creating mechanical, electromagnetic, and thermal noise.

The above examples and implementations are not necessarily inclusive or exclusive of each other and may be combined in any manner that is non-conflicting and otherwise possible, whether they be presented in association with a same, or a different, embodiment or example or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above examples implementations are illustrative rather than limiting.

BRIEF DESCRIPTION OF THE DRAWINGS

FIG. 1 is a simplified diagram of a radar/wireless backscattering sensor system according to an example.

FIG. 2 is a simplified diagram of a sensor array according to an example.

FIG. 3 is a simplified diagram of a system according to an example.

FIG. 4 is a detailed diagram of a hardware apparatus according to an example.

FIG. 5 is a simplified diagram of a hub according to an example.

FIG. 7 is a simplified diagram of a mini node according to an example.

FIG. 11 is a simplified diagram illustrating senior activities of daily living (ADL) categories in an example.

FIG. 12 is a simplified diagram illustrating an activities list according to an example.

DETAILED DESCRIPTION OF THE EXAMPLES

Figure 6:
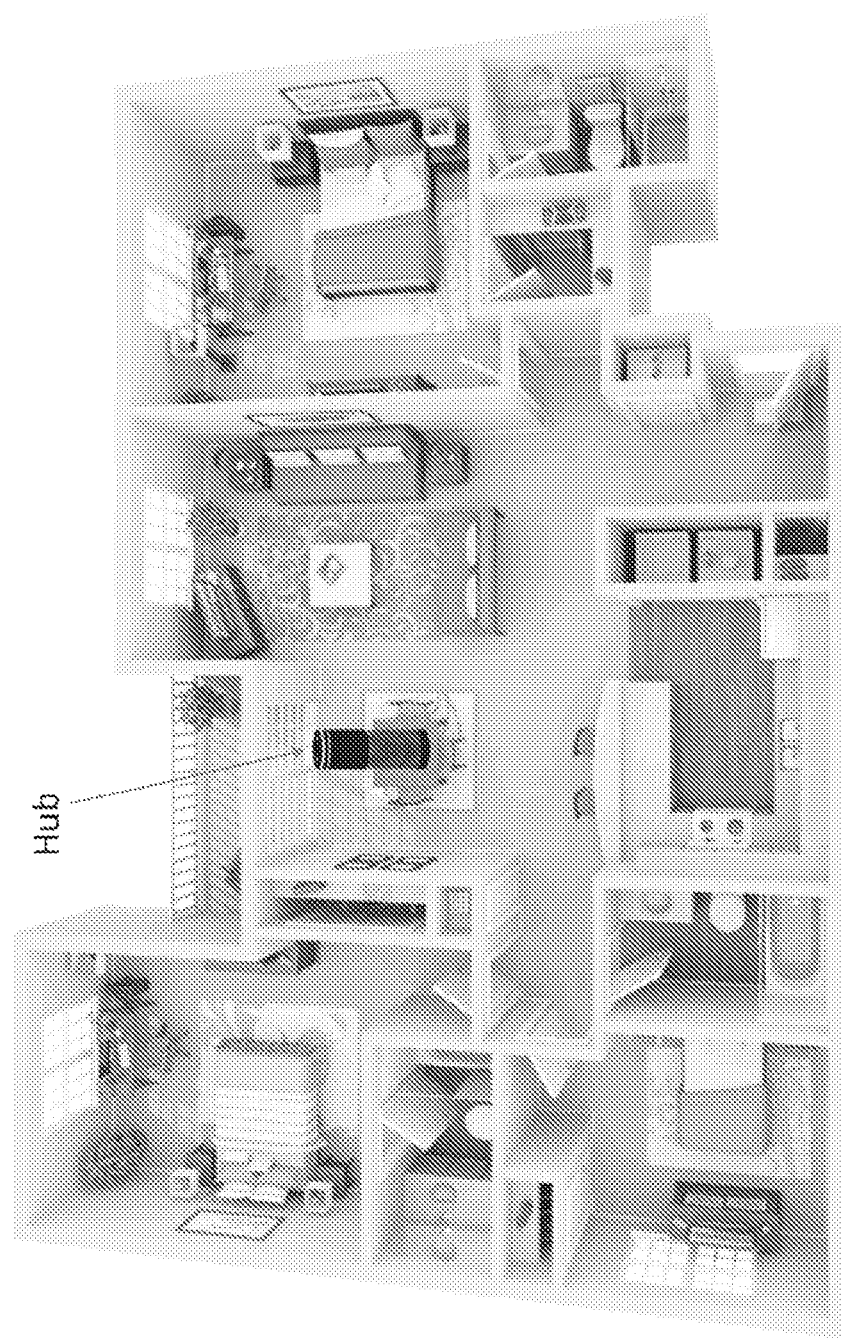
FIG. 6 is a simplified diagram of a hub in a spatial region according to an example of an example of a device.

Techniques, including a method and system, for processing signals using artificial intelligence techniques to monitor, detect, and act on activities are provided. In an example, the signals can be from both active and passive sensors, among others. Merely by way of examples, various applications can include daily life, and others.

FIG. 1 is a simplified diagram of a radar/wireless backscattering sensor system 100 according to an example. This diagram is merely an example, which should not unduly limit the scope of the claims herein. In an example, the sensor system 100 is a wireless backscattering detection system. The system 100 has a control line 110 coupled to a processing device 120, the control line 110 being configured with a switch to trigger an initiation of a wireless signal. In an example, the system 100 has a waveform pattern generator 130 coupled to the control line 110. The system 100 has an RF transmitter/receiver 140 coupled to the waveform pattern generator 130. The system 100 has a transmitting antenna 150 and a receiving antenna 160. In an example, the system 100 has a transmitting antenna 150 coupled to the RF transmitter/receiver 140, which is coupled to an RF receiving antenna 160. In an example, the system 100 has an analog front end 170 comprising a filter. In an example, an analog-to-digital converter 180 is coupled to the analog front end 170. The system 100 has a signal-processing device 120 coupled to the analog-to-digital converter 180. In an example, the system 100 has an artificial intelligence processor coupled to the signal-processing device 120. The AI processor is configured to process information associated with a backscattered signal captured from the RF receiving antenna 160. Further details of the present system can be found throughout the specification and more particularly below.

Antenna

In an example, multiple aspects of antenna design can improve the performance of the activities of daily life ("ADL") system. For example, in scanning mode, the present technique continuously looks for moving human targets (or user) to extract ADL or a fall. Since these can happen anywhere in the spatial region of a home, the present system has antennas that have wide field of view. Once the human target is identified, the technique focuses signals coming only from that particular target and attenuate returns from all other targets. This can be done by first estimating location of the target using wide field-of-view antennas and then focusing RF energy on the specific target of interest once it has been identified. In an example, the technique can either electronically switches a different antenna that has narrow field of view or can use beam-forming techniques to simultaneously transmit waves from multiple transmit antennae and control their phase such that the RF energy constructively builds around the target of interest whereas it destructively cancels everywhere else. This return will be much cleaner and can boost the performance of the ADL+fall+vital sign sensors.

Another example considers the layout of the antennas itself. In an example, the technique places transmit and receive antennas in various physical configurations (Uniform Linear Array (ULA), circular, square, etc.), that can help establish the direction from which the radar signal returns by comparing phases of the same radar signal at different receiving antennas. The configurations can play a role because different configurations enable direction of arrival measurements from different dimensions. For example, when a human target falls, the vertical angle of arrival changes from top to bottom; therefore a vertical ULA is better suited to capture that information. Likewise during walking, horizontal angle of arrival of the signal varies more; therefore it makes sense to use horizontal ULA, which is more sensitive and therefore can provide additional information for the system's algorithm. Of course, there can be other variations, modifications, and alternatives.

RF Unit

In an example, the wireless RF unit (radar) can be either pulsed doppler radar or frequency modulated continuous wave (FMCW) or continuous wave doppler (CW). In an example, on the transmit side the RF unit will have standard RF units like Voltage Controlled Oscillator (VCO), Phase Locked Loop (PLL), among others. On the receive side the RF unit can have matched filter, Low Noise Amplifier (LNA), mixer, and other elements. The multiple antennas can be either driven by a single transmit/receive chain by sharing the chain in time or have one of each chain for each of the antennas.

Waveform Unit

In an example, a waveform pattern generator generates control signals that define the type of radar signal that is generated by the radar RF unit. For example, for FMCW, the pattern generator can generate triangular waves of specific slope and period, which will linearly sweep the frequency of the RF unit according to this parameter. For a pulsed doppler radar, the technique will generate pulses of specific width and period, which will modulate the RF output accordingly.

Baseband Unit

In an example, the gain and filter stage filters the radar returns to remove any unwanted signals and then amplifies the remaining signal with different techniques. For example, the present artificial intelligence or AI technique can determine what target is desirably tracked and provide feedback to the AI technique, which will filter out radar return from any and all other signals except for the signal that is desirably tracked. If the human target is moving, the return signal will be fluctuating, in which case the technique applies automatic gain control (AGC) to find the optimal gain, so that the entire dynamic range of analog-to-digital converter (ADC) in the subsequent stage is satisfied. In an example, the return signal is converted to digital samples by analog-to-digital converters, among other front-end elements.

FIG. 2 is a simplified diagram of a sensor array according to an example. This diagram is merely an example, which should not unduly limit the scope of the claims herein. Shown is a sensor array 200. The sensor array 200 may include a plurality of passive sensors 210. In an example, the plurality of passive sensors 210 is spatially disposed in a spatial region of a living area. The sensor array has active sensors, such as one or more radar sensors 220. Additionally, the array 200 has a feedback interface, such as a speaker 230 for calling out to a human target in the spatial region of the living area.

In an example, the present technique is provided to identify various activities in home using a non-wearable. In an example, the technique is the least privacy intrusive as possible and will use sensors that are less intrusive. Examples of sensors can include, without limitation, a wireless backscatter (e.g., radar, Wi-Fi), audio (e.g., microphone array, speaker array), video (e.g., PTZ mounted, stereo), pressure mats, infrared, temperature, ultraviolet, humidity, pressure, smoke, any combination thereof, and others.

Active Sensor for RADAR

In an example, the technique can use wireless backscattering to measure motion of a human, a location, and an environmental state, such as door opening/closing, or other environmental conditions. In an example, the wireless backscattering can also be used to measure a vital sign, such as a heart rate and respiration rate, among others. In an example, the wireless techniques can work in non-line of sight, and are non-intrusive compared to camera or microphone, or others. In an example, a technique can use a radar/backscatter sensor for two purposes such as (1) to find the location of an action; and (2) sense different activities associated with the action. Of course, there can be other variations, modifications, and alternatives.

In an example, the present techniques and system may include a radar system that operates on multiple frequency bands, such as below 10 GHz, around 24 GHz, 60 GHz, 77-81 GHz, among others. In an example, different frequencies interact differently with various objects in an environment. In an example, available signal bandwidth and permissible signal power are also regulated differently at different frequency bands. In an example, the present techniques optimally combine reflections coming from a reflector from multiple frequency bands to achieve large coverage, and/or improve accuracy. Of course, there can be other variations, modifications, and alternatives.

In an example, each radar working at a particular frequency band will be using multiple transmit and receive antennas, as shown. In an example, using these multiple transmitters, the technique can perform transmit beamforming to concentrate radar signal on a particular target. In an example, the technique uses multiple receivers to collect reflected signals coming from various reflectors (e.g., human body, walls). The direction of the reflector with respect to the radar can be found after further processing. In an example, the technique also uses multiple transmitters and receivers to form a virtual array, allowing emulation of the radar array with large element by using a small number of transmitter and receiver chains. The main benefit is to improve the angle resolution without using a large array, saving space and component cost. In an example, different antenna array configurations to improve coverage (using beam forming) or add 3D localization capability (using 2-D array) are included.

In an example using standard radar signal modulation techniques, such as FMCW/UWB, on MIMO radar, the technique first separates signals coming from different ranges and angles. The technique then identifies static reflectors, such as chairs, walls, or other features, from moving ones, such as human targets, pets, or the like. For moving objects that are tracked, the technique further processes signals for each of the reflectors. As an example, the technique uses different techniques to extract raw motion data (e.g., like spectrogram). In an example, the technique applies various filtering processes to extract periodic signals generated by vital signs, such as heart rate, respiration rate, among others. In an example, both the raw motion data and extracted vital signs are passed to a downstream process, where they are combined with data from other sensors, such as radar outputs operating at different frequencies or completely different sensors, to extract higher insights about the environment. Of course, there can be other variations, modifications, and alternatives.

Audio Sensor

In an example, the present technique uses a sensor array that has a multiple microphone array 240. In an example, the microphone array 240 will be used to ascertain the direction of arrival of any audio signal in the environment. In an example, the microphone array 240 in conjunction with other sensors, such as radar sensors 220, will be vital in performing two tasks: 1) it will augment a radar signal to identify various activities (e.g., walking produces a different sound than sitting; if the target is watching TV it is much easier to ascertain it with audio signal); and 2) in case of an emergency like a fall, the technique can use the radar signal to identify the location of the fall and then beamform the microphone array 240 towards that location, so that any audio signal produced by the target can be captured. Of course, there can be other variations, modifications, and alternatives.

Sensor Fusion and Soft Sensors

In addition to a radar sensor, which is considered an active sensor, the present sensor system (e.g., box, boxes) will also have additional passive sensors that capture sound, chemical signature, and other environmental conditions. Each of the sensors captures a different context about the home that the human being tracked is living in or occupying. In an example and as illustrated in FIG. 2, a UV sensor 250 sensor can monitor how often sunlight comes in the room. In an example, light sensors determine a lighting condition of the human's home or living area.

In an example, a microphone array 240 can have many functions, such as use to sense sound in the room, to figure out how long the human has spent watching TV, or how many times they went to bathroom by listening to the sound of a toilet flushing or other audio signature. In an example, the present technique can use creative solutions where it can use the active sensor to find the location of the person and then tune the microphone array 240 to enhance the sound coming from that location only, among other features. In an example, the technique can call the sensors that are derived from the hardware sensors using specific algorithms as software sensors or soft sensors. In this way, the same hardware sensors can be used for many different applications by creating different software sensors. Here the software sensors can combine signals from one or more sensors and then apply sensor fusion and AI techniques to generate the desired output. Of course, there can be other variations, modifications, and alternatives.

Soft Sensor for Detecting Cooking and Eating Habits

In example, radar sensors can determine information about a human's location within a home, like if they are in kitchen area or other location. In an example, when the human target turns on the microwave oven, it generates a specific RF signature that can be tracked. In an example, the technique can combine this information to infer if the human target walked to the kitchen and turned on the microwave. Likewise, when the human target prepares food in the kitchen, he/she can make specific noise like utensils clattering, chopping, or other audio signature. If a human target goes to the kitchen and spends some time in the kitchen, and the present microphone picks up these sounds, the technique can infer that food is cooking or another activity is occurring.

Soft Sensor for Detecting Bathroom Habits

In an example, toileting frequency can be a very valuable indication of one's wellness. The present technique can track if a human went to the bathroom using the radar or other sensing techniques. In an example, additionally, the technique can pick up a sound signature of a toilet flushing. In an example, the technique combines these two pieces of information, which can be correlated to toileting frequency. In an example, similarly, bathing is a unique activity that requires 4-5 minutes of specific movements. By learning those patterns, the technique can figure out one's bathing routines.

Soft Sensor for Detecting Mobile Habits

In an example, different sensors are triggered by different motions of a human target. In an example, radar can detect a human fall by looking at micro doppler patterns generated by different parts of the target during falls. In an example, the technique can also simultaneously hear a fall from microphone arrays and vibration sensors. In an example, the technique can also detect how pace of movement changes for an individual over a long duration by monitoring the location information provided by radar or other sensing technique. In an example, likewise, the technique can gather unstable transfers by analyzing the gait of the target. In an example, the technique can find front door loitering by analyzing the radar signal pattern. In an example, the technique can figure out immobility by analyzing the radar return. In this case, the technique can figure out the target's presence by analyzing the target's vital signs, such as respiration rate or heart rate, or by keeping track of the bread crumb of the target's location trace.

In any and all of the above cases, the technique can also learn about the exact environmental condition that triggered a particular state. For example, the technique can figure out whether a human target was immobile because the target was watching TV or a video for long duration or the target was simply spending a lot of time in their bed. This information can be used to devise incentives to change the target's behavioral pattern for better living.

Soft Sensor for Detecting Vital Signs

In an example, the technique can estimate vital signs of a person by sensing the vibration of the target's body in response to breathing or heartbeat, each of which produces actions resulting in small phase changes in the radar return signals, which can be detected. In an example, the technique will use several signal processing techniques to extract these signals. Of course, there can be other variations, modifications, and alternatives.

In an example, different frequency radio waves interact with an environment differently. Also, phase change due to vital signs (HR, RR) differs by frequency; for example, a phase change for a 77 GHz radar is much higher than for a 10 GHz radar. Thus 77 GHz is more appropriate for estimating heart beat more accurately. But higher frequency typically attenuates much more rapidly with distance. Therefore, lower frequency radar can have a much larger range. By using multi-frequency radar, the present technique can perform these vital trade-offs.

Soft Sensor for Detecting Sleeping Habits

In an example, the present radar sensors can detect motions that are generated during sleep, such as tossing and turning. In an example, radar sensors can also sense vital signs like respiration rate and heart rate as described earlier. In an example, now combining the pattern of toss and turn and different breathing and heartbeat patterns, the technique can effectively monitor the target's sleep. Additionally, the technique can now combine results from passive sensors, such as a thermometer, UV, photo diode, among others, to find correlation between certain sleep patterns and the environmental conditions. In an example, the technique can also use the sleep monitor soft sensor to learn about day/night reversal of sleep and the associated environmental condition by looking at different passive sensors. In an example, the techniques can be valuable in providing feedback to improve the human target's sleep. For example, the technique can determine or learn that certain environmental conditions result in better sleep and prescribe that to improve future sleep.

Soft Sensor for Security Applications

In an example, the technique can repurpose many of the sensors described before for security applications. For a security application, the technique determines where one or more person is located, which can be detected using a presence detection sensor that is built on top of radar signals. In an example, the technique can eliminate one or many false positives triggered by traditional security systems. For example, if a window is suddenly opened, the technique (and system) will look at presence of a human in the vicinity before triggering the alarm. Likewise, a combination of vital signs, movement patterns, among others, can use a biometric to identify any human target. If an unknown human target is detected in the vicinity at a certain time of the day, the technique can trigger an alarm or alert.

In an example, any one of the above sensing techniques can be combined, separated, or integrated. In an example, in addition to radar and audio sensors, other sensors can be provided in the sensor array. Of course, there can be other variations, modifications, and alternatives.

FIG. 3 is a simplified diagram of a system according to an example. This diagram is merely an example and should not unduly limit the scope of the claims herein. As shown, the system has hardware and method (e.g., algorithm), cloud computing, personalized analytics, customer engagement, and an API to various partners, such as police, medical, the user or patient, and others. Further details of the present system can be found throughout the present specification and more particularly below.

FIG. 4 is a detailed diagram of a hardware apparatus according to an example. This diagram is merely an example and should not unduly limit the scope of the claims herein. As shown, the hardware unit includes at least a hub device, node, and mobile node, each of which will be described in more detail below.

FIG. 5 is a simplified diagram of a hub according to an example. This diagram is merely an example and should not unduly limit the scope of the claims herein. In an example, the hub may include various sensing devices. The sensing devices include, among others, a radar, a Wi-Fi, a Bluetooth, a Zigbee sniffer, a microphone and speakers, a smoke detector, a temperature detector, a humidity detector, a UV detector, a pressure detector, MEMS (e.g., accelerometer, gyroscope, and compass), a UWB sensors (for finding locations of all the deployed elements relative to each other), among others. In an example, the hub is a gateway to internet via Wi-Fi, GSM, Ethernet, landline, or other technique. The hub also connects to other units (Mini Node/Mobile Node) via Bluetooth, Wi-Fi, Zigbee, UWB and coordinates them with each other. In an example, certain data processing, such as noise removal or feature extraction to reduce the amount of data uploaded to the cloud, is included. In an example, the hub alone can be sufficient to cover a small living space. In an example, the hub is deployed as a single device in a desirable location (e.g., middle of the living space) so that it has good connectivity to all other units. An example of such deployment is provided in the FIG. 6.

FIG. 6 is a simplified diagram of a hub in a spatial region according to an example. This diagram is merely an example and should not unduly limit the scope of the claims herein. As shown, the hub is deployed in the middle of the living space in a house.

FIG. 7 is a simplified diagram of a mini node according to an example. This diagram is merely an example and should not unduly limit the scope of the claims herein. As shown, the system has sensors, which is a subset of sensors in the hub. The sensors are configured in various spatial locations to improve coverage area and improve accuracy for detection of critical events (e.g., fall, someone calling for help). The sensors also communicate with the hub via Wi-Fi, Bluetooth, ZigBee or UWB, or another technique known in the art. Additionally, the sensors or each mini node are deployed in a bathroom, where chances of a fall are high; a kitchen, where eating habits can be learned by listening to sounds, RF waves, or vibrations; or a perimeter of the living space that will allow the system to learn an approximate map of the space under consideration, among other locations. Additionally, each of the mini modes can save power and costs by adding more complexity on the hub. This can enable the system to operate on battery for extended periods. For example, each of the nodes can have only single-antenna Wi-Fi, and the hub could have multiple antennas for Wi-Fi—based sensing. Additionally, each of the nodes uses simpler radar (e.g., single antenna doppler) vs MIMO FMCW in the HUB. Additionally, each node can be configured with a single microphone whereas the hub can have an array of microphones. Of course, there can be other variations, modifications, and alternatives.

Figure 8:
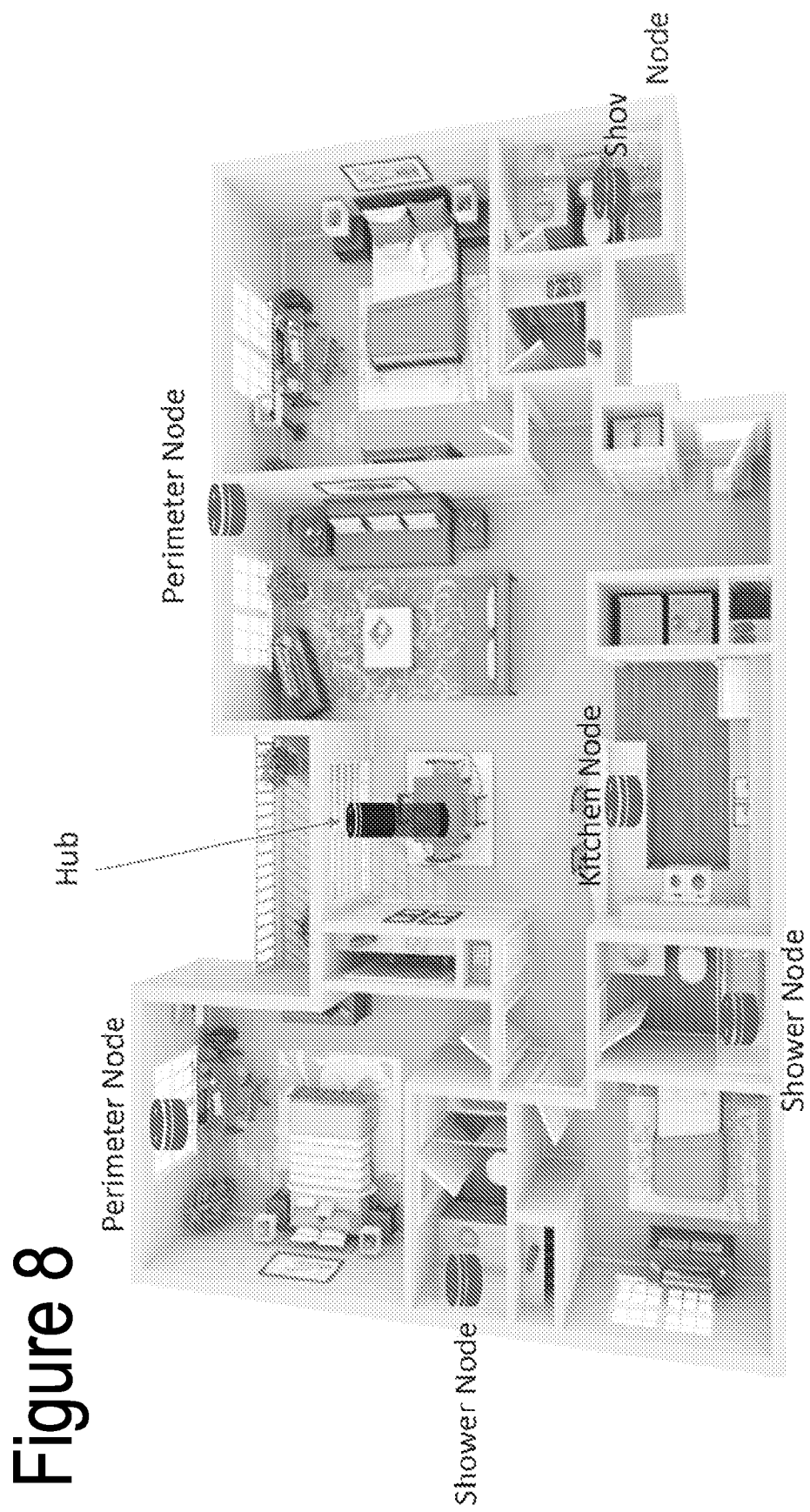
FIG. 8 is a simplified diagram of a mini mode in a spatial region according to an example.

FIG. 8 is a simplified diagram of a mini mode in a spatial region according to an example. This diagram is merely an example and should not unduly limit the scope of the claims herein. As shown, each node is configured in a kitchen, shower, perimeter, or other location.

Figure 9:
FIG. 9 is a simplified diagram of a mobile node according to an example.

FIG. 9 is a simplified diagram of a mobile node according to an example. This diagram is merely an example and should not unduly limit the scope of the claims herein. In an example, each mobile node is a subset of sensors in the hub. The mobile node sensors include a camera such as red, green, blue (RGB) or infrared (IR). In an example, each of the nodes and hub collaboratively figure out interesting events and pass that information to the mobile node. The technique then goes to the location and probes further. In an example, the camera can be useful to visually find what is going on in the location. In an example, freewill patrolling can be used to detect anything unusual or to refine details of the map created based on perimeter nodes. In an example, onboard UWB can enable precise localization of the mobile node, which can also enable wireless tomography, where the precise RGB and wireless map of the living space is determined.

Figure 10:
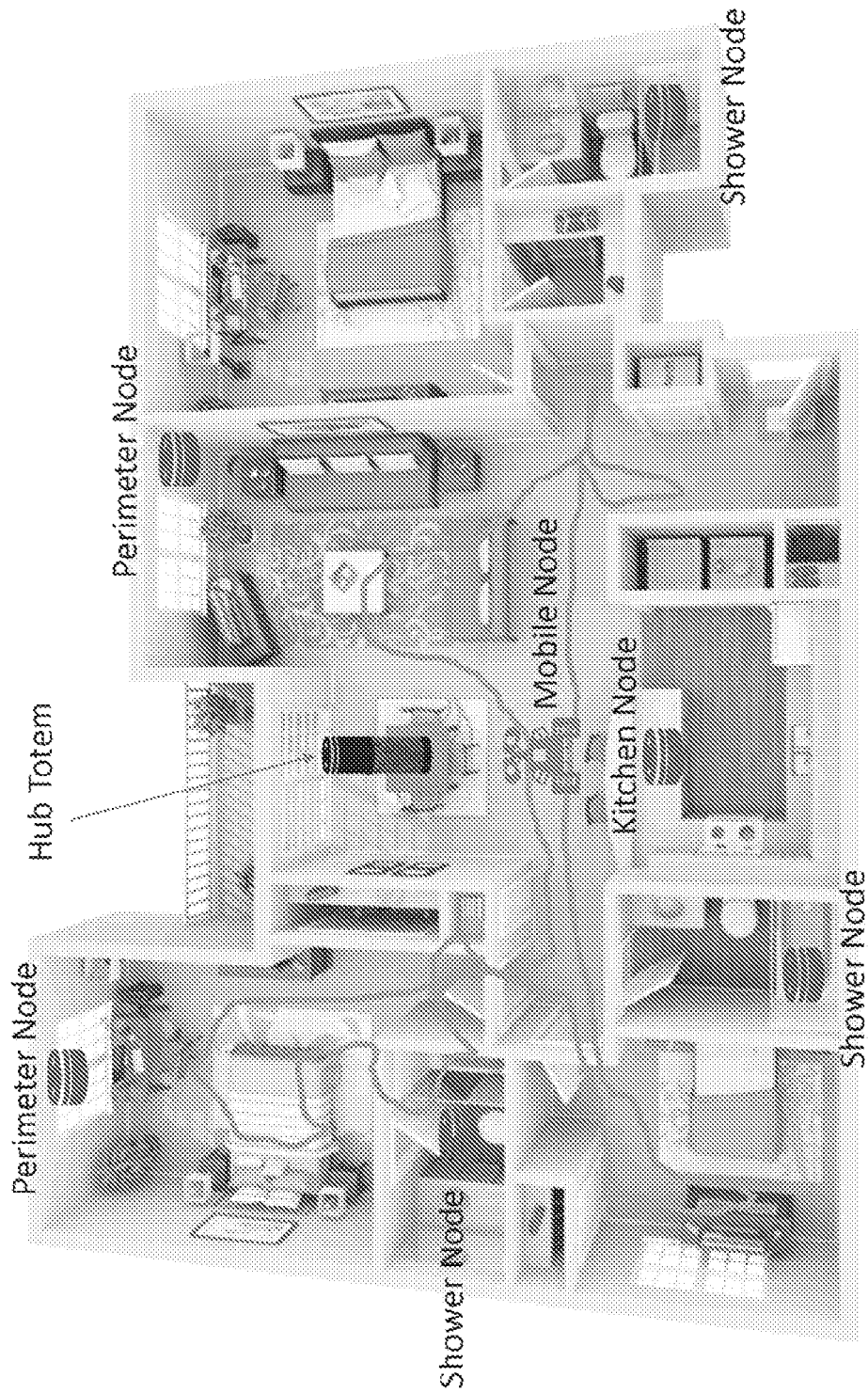
FIG. 10 is a simplified diagram of a mobile mode in a spatial region according to an example.

FIG. 10 is a simplified diagram of a mobile mode in a spatial region according to an example. This diagram is merely an example and should not unduly limit the scope of the claims herein. As show, the mobile node, such as a mobile phone or smart phone or other movable device, can physically move throughout the spatial location. The mobile node can also be a drone or other device.

In an example, the technique transfers learned information and activity information to third parties. The technique teaches itself to learn high-level behaviors that are indicative of a person's welfare using artificial intelligence techniques. In an example, the present technique then generates a summary of such activities and sends it to the human's loved ones, caretaker, or even emergency response team, depending on the urgency of the situation. For example, for regular days, the technique can simply send a short summary like, "Your mom had a routine activity today", or "She was much less active today." In an example, where the human has a caretaker visiting a few times a week, the technique can send a notification to them, such as "It seems she struggled more yesterday", so that the caretaker can pay a visit to make sure everything is fine. Alternatively, the technique can be used for more acute events like a fall, shortness of breathing, or others, that need quick attention. In these scenarios, the technique can notify a medical response team to provide immediate help. Of course, there can be other variations, modifications, and alternatives.

FIG. 11 is a simplified diagram illustrating senior ADL categories in an example. As shown, the present technique can categorize a human target with the listed ADLs, among others.

FIG. 12 is a simplified diagram illustrating an activity list according to an example. As shown, the present technique can determine activities of a human target with any one of the activities listed.

In an example, the present technique can also identify a rare event. In an example, the technique identifies when a senior human falls inside a home with no one around. In an example, the technique is robust, without any false negatives. In an example, the technique looks at a sequence of events occurring before a potential fall and a sequence occurring after a potential fall. In an example, the technique combines the contextual information to robustly determine if a fall has occurred. Of course, there can be other variations, modifications, and alternatives.

In an example, the technique also detects and measures vital signs of each human target by a continuous, non-intrusive method. In an example, the vital signs of interest include a heart rate and a respiratory rate, which can provide valuable information about the human's wellness. Additionally, the heart rate and respiratory rate can also be used to identify a particular person, if more than two target humans are living in a home. Of course, there can be other variations, modifications, and alternatives.

By understanding the context of how the target human (e.g., elderly) is doing, the technique can also provide valuable feedback directly to the elderly using a voice interface. For example, the technique can sense a mood of the human based on a sequence of activities and vital signs of the human and then ask, "Hi, do you want me to call your son?" Based upon the feedback from the human, the technique can help connect to a third party (or loved one) if their answer is positive. In still another example, the technique can provide cognitive behavior therapy to the target human based on the sensed activity of daily living (ADL) so that the target human can improve the ADL such as improving his or her sleep when the cognitive behavioral therapy is implemented by the target human. Of course, there can be other alternatives, variations, and modifications.

Having described various embodiments, examples, and implementations, it should be apparent to those skilled in the relevant art that the foregoing is illustrative only and not limiting, having been presented by way of example only. Many other schemes for distributing functions among the various functional elements of the illustrated embodiment or example are possible. The functions of any element may be carried out in various ways in alternative embodiments or examples.

Also, the functions of several elements may, in alternative embodiments or examples, be carried out by fewer, or a single, element. Similarly, in some embodiments, any functional element may perform fewer, or different, operations than those described with respect to the illustrated embodiment or example. Also, functional elements shown as distinct for purposes of illustration may be incorporated within other functional elements in a particular implementation. Also, the sequencing of functions or portions of functions generally may be altered. Certain functional elements, files, data structures, and so on may be described in the illustrated embodiments as located in system memory of a particular or hub. In other embodiments, however, they may be located on, or distributed across, systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of files may be used and various described data structures of files may be combined or otherwise arranged.

In other examples, combinations or sub-combinations of the above disclosed examples can be beneficially made. Some embodiments may incorporate smart speaker interface and controls, such as currently provided by Google Home, Amazon Alexa, Apple HomePod and others. For example, using the sensor and AI techniques described above, the device may perform appropriate actions. As examples of this, if the device determines that the user has fallen down and cannot get up, the device may call for help, turn on all the lights, and/or unlock the doors; if the device determines that the user is cooking, the device may turn on an exhaust fan, increase sensitivity for a smoke detector, and/or turn on the lights in the kitchen; if the device determines that the user is alone watching television, the device may turn off lights in other rooms; turn down the light in the room the user is in; and turn off music playing in other rooms; and the like. In light of the present disclosure, one of ordinary skill in the art should recognize many other types of actions that may be performed based upon the user sensed activity.

The block diagrams of the architecture and flow charts are grouped for ease of understanding. However it should be understood that combinations of blocks, additions of new blocks, re-arrangement of blocks, and the like are contemplated in alternative embodiments.

The specification and drawings are, accordingly, to be regarded in an illustrative rather than a restrictive sense. It will, however, be evident that various modifications and changes may be made thereunto without departing from the broader spirit and scope of the embodiments of the invention as set forth in the claims.

Techniques related to a method and system for processing UWB and FMCW signals using a plurality of antenna array are provided. In particular, the inventive subject matter provides an apparatus using a thermal and mechanical confirmation to allow heat generating multi-core processors and artificial intelligence processes to operate without forced air convection. Merely by way of example, various applications can include daily life, and others.

In an example, the present technique provides an apparatus configured to generate RF energy for spatial sensing. The apparatus has a housing comprising a base portion, an exterior side, and an upper portion. In an example, the housing has an inner region and an exterior region enclosing the inner region. In an example, the apparatus has a plurality of openings configured on the exterior region to allow air and thermal energy to flow through the openings. In an example, the apparatus has a processing device comprising a semiconductor substrate having a processing block, a memory block, and an interface block. In an example, the processing device is disposed on the base portion and coupled to a power source, and operable to generate thermal energy of at least 5 Watts to about 16 Watts. In an example, the apparatus has a radar configured within the interior region and having a plurality of apertures, and disposed in the upper portion of the housing. In an example, the radar has a plurality of receive antennae coupled to an RF receiver and a plurality of transmit antennae coupled to an RF generator.

In an example, the apparatus has a natural convection spatial flow path initiating from the processing device through the plurality of openings, and through the radar using the plurality of apertures to maintain an interior region of the housing within a temperature of 10 degrees C. to no greater than 90 degrees C., while being substantially free from an electromagnetic noise, mechanical noise, and a stream of forced convection. In an example, the apparatus has a heat sink region coupled to an upper portion of the housing and configured within a region of the natural convection spatial flow path to maintain the interior region within the temperature of 10 degrees C. to no greater than 90 degrees C. In an example, the temperature can have other ranges up to 80 degrees Celsius, 85 degrees Celsius, and 100 degrees Celsius.

In an example, the processing device is low power, and ranges from about 5 Watts to about 14 Watts. In an example, the housing comprises a polymeric material having a melting temperature of 90 degrees Celsius to 105 degrees Celsius. In an example, the processing device is provided in a processor. In an example, the plurality of openings has an area of 30 to 90% of a total area of the exterior region. In an example, the apparatus does not have a fan device, which creates vibration that will reduce accuracy of the radar. Further, absence of a fan device also reduces noise generation that will interfere with a person's sleep.

In an example, the housing is configured as a shape of a cylinder, or other shape, such as pyramid, rectangular, box shaped, or others. In an example, the housing is configured as a shape of a multi-sided object.

In an example, the apparatus has a heat shield configured within a vicinity of the radar to divert thermal energy from the processing device into the natural convection spatial flow path. In an example, the apparatus has a heat shield configured within a vicinity of the radar to divert thermal energy from the processing device into the natural convection spatial flow path; and an insulating material provided between the heat shield and the radar.

In an example, an example provides an apparatus configured to generate RF energy for a spatial sensing. In an example, the apparatus has a housing comprising a base portion, an exterior side, a lower portion, and an upper portion. In an example, the housing has an inner region and an exterior region enclosing the inner region. In an example, the apparatus has a plurality of openings configured on the exterior region.

In an example, the apparatus has a processing device comprising a semiconductor substrate having a processing block, a memory block, and an interface block. In an example, the processing device is disposed on the upper portion and coupled to a power source, and operable to generate thermal energy of at least 5 Watts to about 16 Watts. In an example, the apparatus has a radar configured within the interior region and having a plurality of apertures, and disposed in the lower portion of the housing. In an example, the radar has a plurality of receive antennae coupled to an RF receiver and a plurality of transmit antennae coupled to an RF generator.

In an example, the apparatus has a natural convection spatial flow path initiating from the processing device through the plurality of openings, and through the radar using the plurality of apertures to maintain an interior region of the housing within a temperature of 10 degrees C. to no greater than 90 degrees C., while being substantially free from an electromagnetic noise, mechanical noise, and a stream of forced convection; and a heat sink region coupled to an upper portion of the housing and configured within a region of the natural convection spatial flow path to maintain the interior region within a predetermined temperature range such as the temperature of 10 degrees C. to no greater than 90 degrees C.

In an example, the processing device is low power, and ranges from about 5 Watts to about 14 Watts. In an example, the housing comprises a polymeric material having a melting temperature of 90 degrees Celsius to 120 degrees Celsius. In an example, the processing device is provided in a processor. In an example, the plurality of openings has an area of 30 to 90% of a total area of the exterior region. In an example, the apparatus does not have a fan device that creates convective flow.

In an example, the housing is configured as a shape of cylinder or other shape. In an example, the housing is configured as a shape of a multi-sided object.

In an example, the apparatus has a heat shield configured within a vicinity of the radar to divert thermal energy from the processing device into the natural convection spatial flow path. In an example, the apparatus has a heat shield configured within a vicinity of the radar to divert thermal energy from the processing device into the natural convection spatial flow path; and an insulating material provided between the heat shield and the radar.

Further details can be found throughout the present specification and more particularly below.

Figure 13:
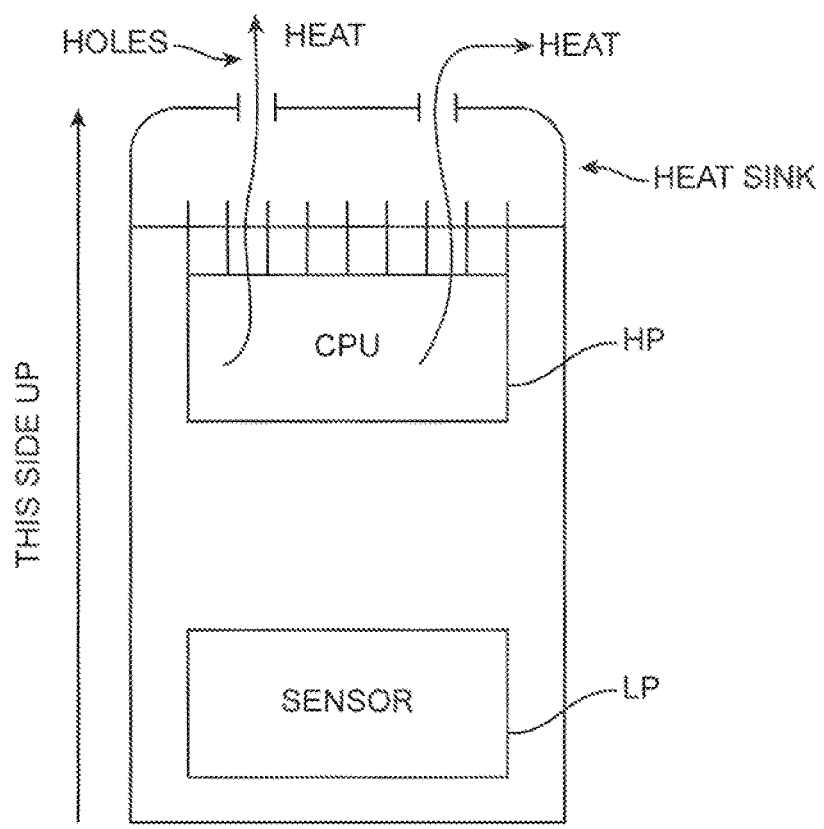
FIG. 13 is a simplified diagram of a wireless sensing and transmitting system according to an example.

FIG. 13 is a simplified diagram of a wireless sensing and transmitting system according to an example. As shown, the apparatus has a sensor (e.g., radar) positioned below a processor, which is higher relative to a direction of gravity than the sensor. Each of the sensor and processor are fitted within housing. The housing has an upper region including a plurality of openings, each of which allows natural convection and thermal energy to flow through the openings. The apparatus has a heat sink positioned overlying the processor.

In an example, thermal energy is generated by the processor and such energy flows outwardly and up via natural convection.

In an example, the sensor has RF transmitting and receiving antenna and generators.

As shown, the apparatus is free from any fans or other mechanical devices that lead to noise and interference of the RF signals.

Figure 14:
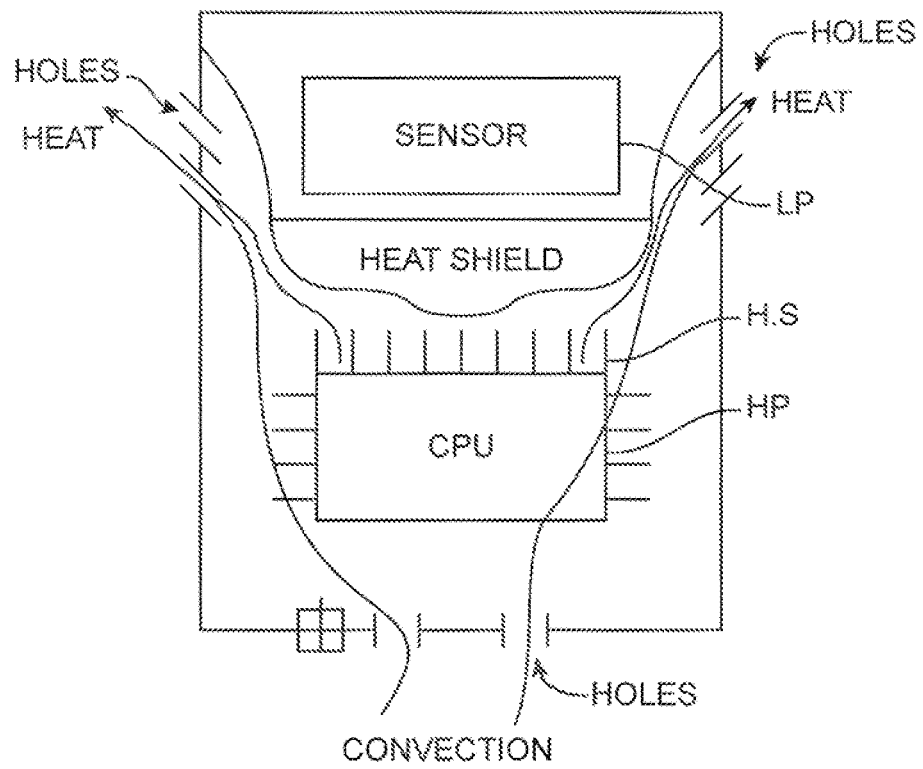
FIG. 14 is a simplified diagram of a wireless sensing and transmitting system according to an example.

FIG. 14 is a simplified diagram of a wireless sensing and transmitting system according to an example. As shown, the processor is positioned below the sensor. The sensor and processor are separated from each other by an insulating material, e.g., a heat shield. Thermal energy flows from the processor and traverses out through a plurality of openings in the housing before interacting with the sensor.

In an example, the sensor has RF transmitting and receiving antenna and generators.

In an example, thermal energy is blocked and separated from the sensor by the insulating material and flow path, which allows thermal energy to traverse through openings underlying the sensor without heating the sensor.

As shown, the apparatus is free from any fans or other mechanical devices that lead to noise and interference of the RF signals.

Figure 15:
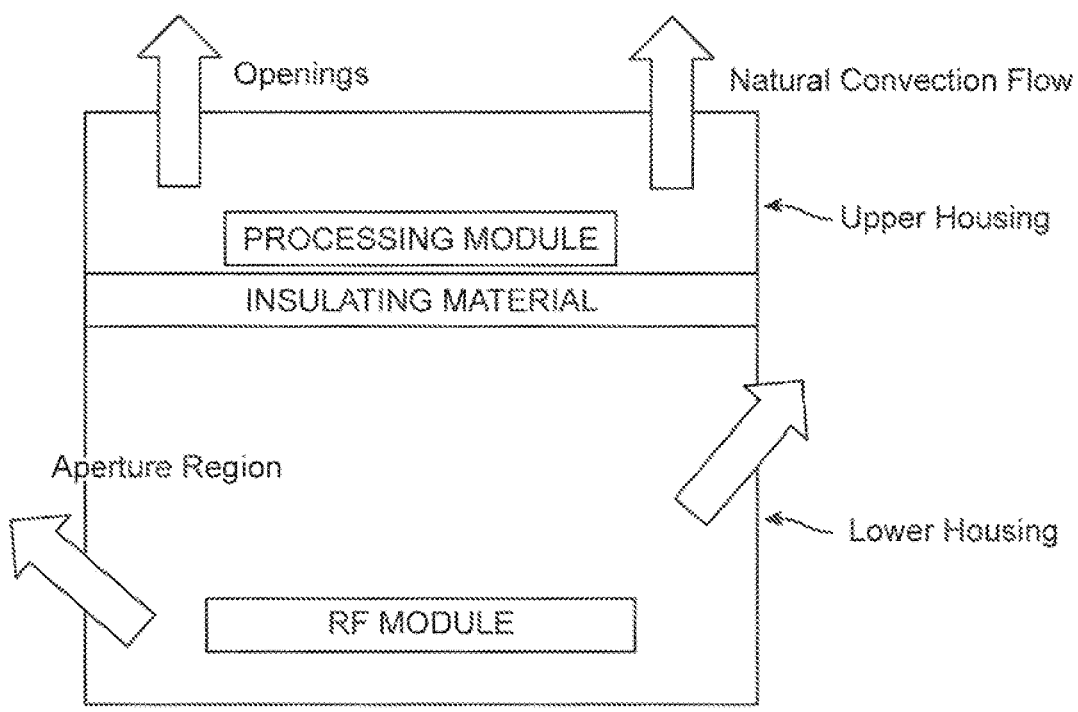
FIG. 15 is a simplified diagram of a wireless sensing and transmitting system according to an example.

FIG. 15 is a simplified diagram of a wireless sensing and transmitting system according to an example. In an example, an apparatus is configured to generate RF energy for a spatial sensing. In an example, the apparatus has a housing comprising a base portion, an exterior side, a lower portion, and an upper portion. In an example, the housing has an inner region and an exterior region enclosing the inner region. In an example, the apparatus has a plurality of openings configured on the exterior region.

In an example, the apparatus has a processing device comprising a semiconductor substrate having a processing block, a memory block, and an interface block. In an example, the processing device is disposed on the upper portion and coupled to a power source, and operable to generate thermal energy of at least 5 Watts to about 16 Watts. In an example, the apparatus has a radar configured within the interior region and having a plurality of apertures, and disposed in the lower portion of the housing. In an example, the radar has a plurality of receive antennae coupled to an RF receiver and a plurality of transmit antennae coupled to an RF generator.

In an example, the apparatus has a first natural convection spatial flow path (see arrows pointing vertically) initiating from the processing device through the plurality of openings, and a second natural convective spatial flow path (see arrows pointed at angles) from the radar through the plurality of apertures to maintain an interior region of the housing within a temperature of 10 degrees C. to no greater than 90 degrees C., while being substantially free from electromagnetic noise, mechanical noise, and a stream of forced convection; and a heat sink region coupled to an upper portion of the housing and configured within a region of the natural convection spatial flow path to maintain the interior region within a predetermined temperature range such as the temperature range of 10 degrees C. to no greater than 90 degrees C.

Figure 16:
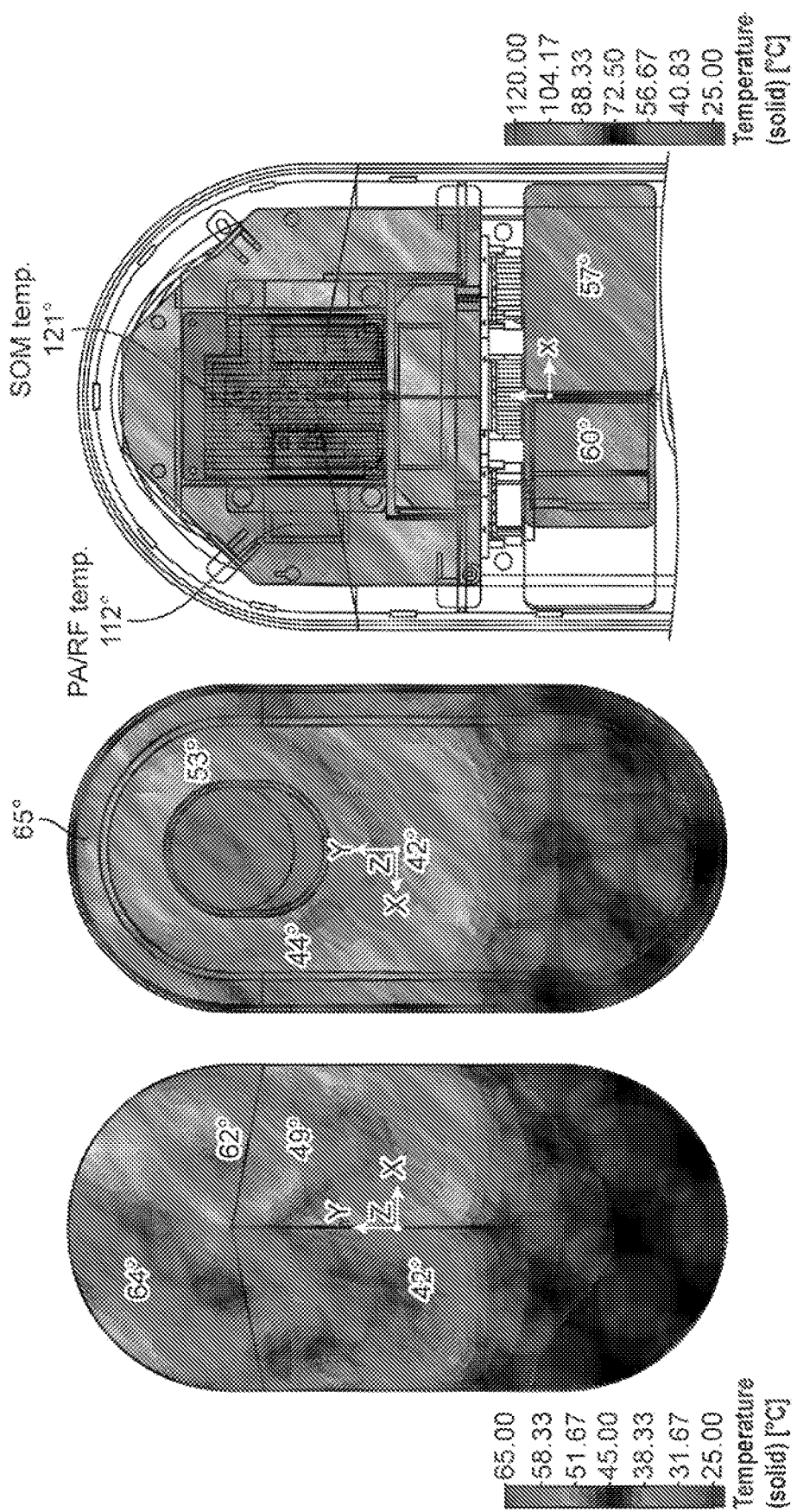
FIGS. 16 and 17 are illustrations of simulations of using the present technique according to an example.
Figure 17:
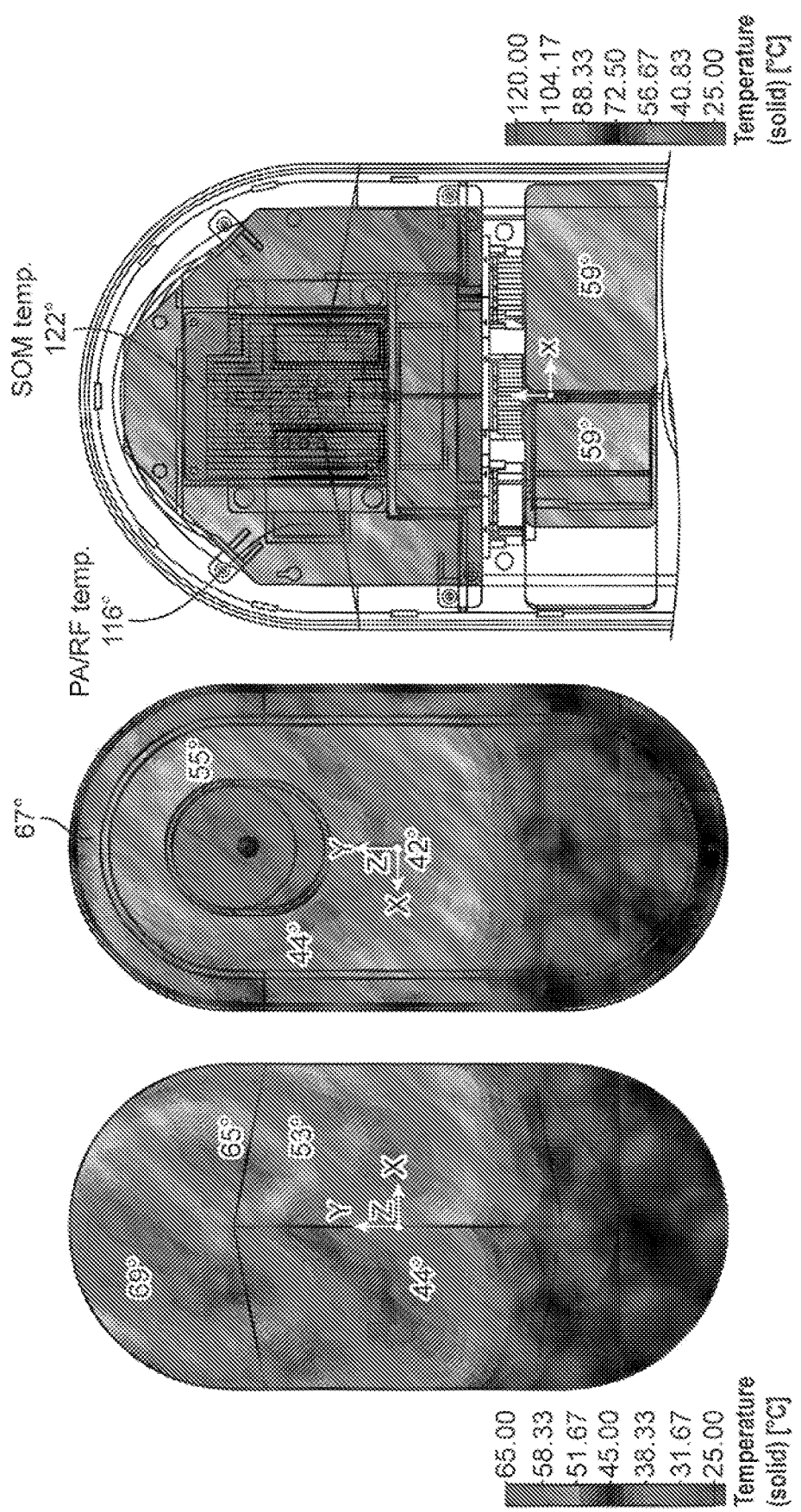

To prove the operation, experiments were performed, as illustrated by FIGS. 16 and 17. As shown, experiments were performed for illustrating heat transfer using conduction, natural convection, and radiation as driving the thermal energy. As shown in each of the FIGS. 16 and 17, a first thermal illustration (on left hand side) shows a thermal cross section along a cross region of an apparatus; a second thermal illustration (in center) shows a thermal cross section along a cross region of the apparatus (which is rotating 180 degrees from the first thermal image), and a mechanical view cross section (on right hand side) illustrating the system of module, system-on-module (SOM), and underlying RF components in the apparatus.

In an example, a power budget was implemented for a main board of 4 Watts (including RF integrated circuit devices) and a SOM for an artificial intelligence inference engine integrated circuit of 6 Watts. Each of the RF components was about 1 Watt (3 Watts total for three components). The ambient temperature was 25 degrees Celsius, and thermal pads 13 Watt/m-K between the SOM components inside the shield can and the shield can; 13 Watt/m-K between the shield can and the heatsink; 13 W/m-K between the RF components and the main board. In these experiments, the configuration in FIGS. 1 and 3 were implemented.

As shown in the Figures, the lower region has been maintained at 25 degrees Celsius to about 85 degrees Celsius, where the RF components are spatially placed. Overlying the RF components, which is the upper region, we had higher temperatures, but maintained within a region a temperature not exceeding 90 degrees Celsius. Of course, the SOM and related components themselves have higher temperatures.

Accordingly, the temperature-sensitive RF components are capable of transmitting RF signals and receiving backscattered signals without interference of mechanical and/or electromagnetic noise from a mechanical fan or other similar mechanical device configured to provide convective forces to remove thermal energy.

Having described various embodiments, examples, and implementations, it should be apparent to those skilled in the relevant art that the foregoing is illustrative only and not limiting, having been presented by way of example only. Many other schemes for distributing functions among the various functional elements of the illustrated embodiment or example are possible. The functions of any element may be carried out in various ways in alternative embodiments or examples.

Also, the functions of several elements may, in alternative embodiments or examples, be carried out by fewer, or a single, element. Similarly, in some examples, any functional element may perform fewer, or different, operations than those described with respect to the illustrated or example. Also, functional elements shown as distinct for purposes of illustration may be incorporated within other functional elements in a particular implementation. In other examples, however, they may be located on, or distributed across, systems or other platforms that are co-located and/or remote from each other. For example, any one or more of data files or data structures described as co-located on and "local" to a server or other computer may be in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures of files may be used, and various described data structures of files may be combined or otherwise arranged.

Figure 18:
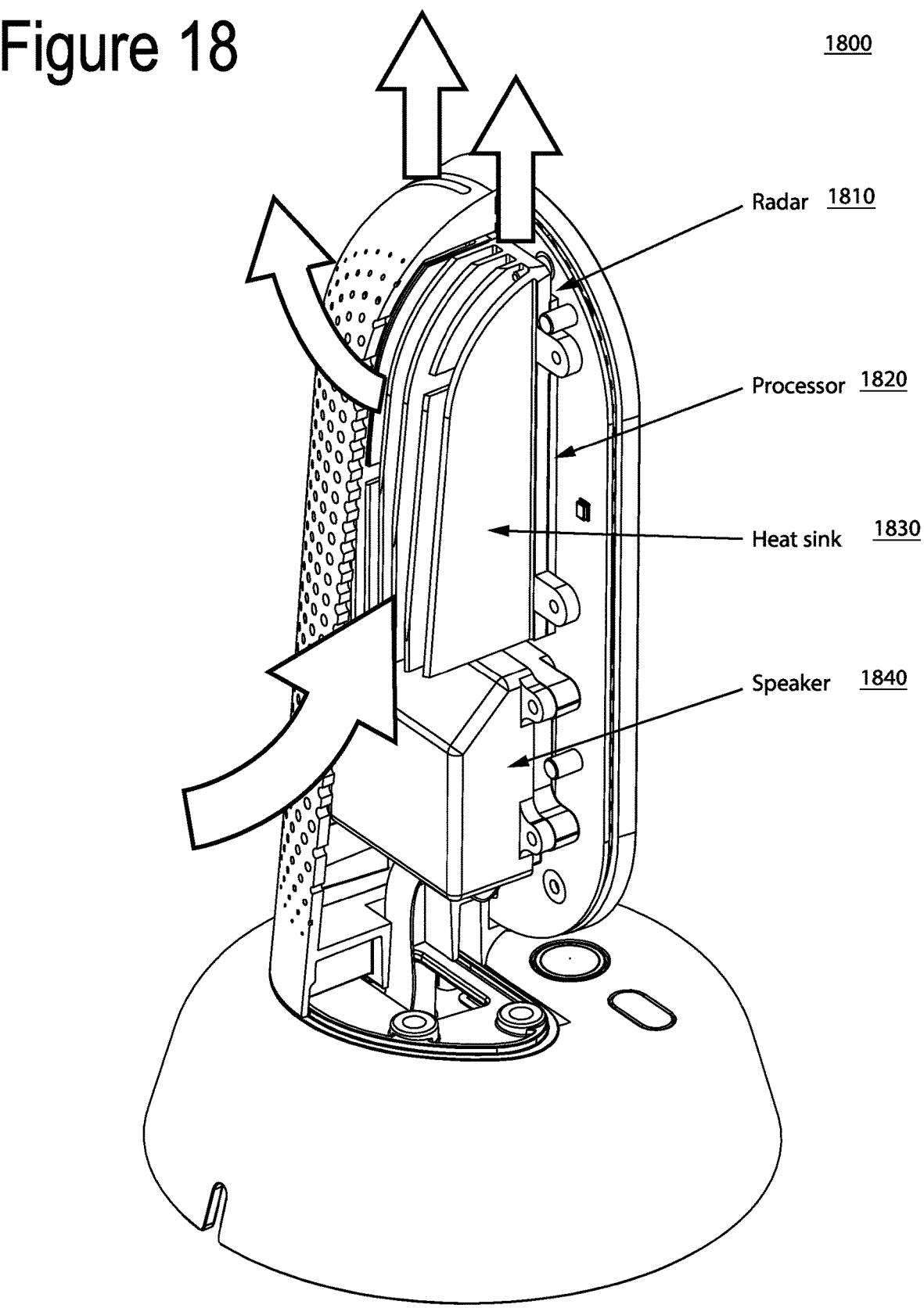
FIG. 18 is a diagram of a wireless sensing and transmitting system according to an example.

FIG. 18 illustrates an example of an apparatus 1800. The apparatus 1800 may include a housing with a plurality of holes to enable air to flow through the housing and exit the housing. The housing may also have or alternatively have one or more slots on a top of the housing for air exhaust. Within the housing, the apparatus 1800 comprises a radar 1810, at least one processor 1820 communicatively coupled to the radar 1810, a heat sink 1830 mounted to the at least one processor 1820 and the radar 1810, and a speaker 1840. The at least one processor 1820 may including a graphics processing unit or other processor optimized to handle artificial intelligence calculations. The heat sink 1830 may include multiple fins oriented vertically to draw heat away from the radar 1810 and the at least one processor 1820 and radiate that heat into a convection flow path. In an example, the heat sink 1830 may include a plurality of flat planar fins that are parallel with one another with a linear edge on one end and an arcuate edge on the opposite end. An air gap is disposed between adjacent fins. The convection flow path pulls air through at least one of the plurality of holes and up along the fins and exits the housing through at least one of the plurality of holes and/or slots.

As mentioned above, the at least one processor 1820 and the radar 1810 can determine vital signs of a human using backscattered radar signals. The determined vital signs can determine if the human is sleeping or awake. For example, even if the person is lying in a bed, determined vital signs may indicate the human is awake. The at least one processor 1820 can employ one or more AI algorithms on the backscattered data to determine the vital sign.

In other examples, combinations or sub-combinations of the above disclosed embodiments of the invention can be beneficially made. The block diagrams of the architecture and flow charts are grouped for ease of understanding. However, combinations of blocks, additions of new blocks, re-arrangement of blocks, and the like are contemplated in alternative embodiments.

The following examples describe various embodiments of methods, machine-readable media, and systems (e.g., machines, devices, or other apparatus) discussed herein.

1. An apparatus for sleep monitoring, comprising:
 a housing having an inner region and an exterior region enclosing the inner region;
 a plurality of openings configured on the exterior region and that communicate with the inner region;
 radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components within the inner region;
 at least one processor within the inner region;
 at least one non-transitory computer-readable medium within the inner region comprising instructions to cause the at least one processor to:
  (i) determine a parameter associated with sleep of an individual based on the received backscattered RF signals; and
  (ii) prescribe an action that, when carried out, modifies the parameter, resulting in an improvement of the sleep of the individual; and
 a natural convection spatial flow path flowing from the inner region and through at least one of the plurality of openings to the exterior region to draw heat from the at least one processor and the RF components without use of a fan, thereby avoiding fan-produced noise and vibration.

2. The apparatus of example 1, further comprising a heat sink having a plurality of fins, the heat sink coupled to the at least one processor and the RF components and wherein the natural convection spatial flow path flows along and between adjacent fins.

3. The apparatus of any of the preceding examples, wherein the at least one processor includes a processor optimized for artificial intelligence algorithms.

4. The apparatus of any of the preceding examples, further comprising a speaker located beneath the at least one processor and the RF components.

5. The apparatus of any of the preceding examples, wherein the parameter associated with the sleep is determined based on a change in the backscattered signal.

6. The apparatus of any of the preceding examples, wherein the change in the backscattered signal is caused by a vibration of at least a portion of a body of the individual and thereby the backscattered signal indicates that the vibration has occurred.

7. The apparatus of any of the preceding examples, wherein the parameter associated with the sleep comprises a vital sign that is determined based at least in part on the vibration.

8. The apparatus of any of the preceding examples, further comprising a microphone that receives an audio signal from the individual or from an environment in which the individual is sleeping.

9. The apparatus of any of the preceding examples, wherein the instructions further cause the at least one processor to associate the audio signal with a factor that affects the sleep of the individual.

10. An apparatus for sleep monitoring, comprising:
 a housing having an inner region and an exterior region enclosing the inner region;
 a plurality of openings configured on the exterior region and fluidly coupled to the inner region;
 radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
 at least one processor within the inner region;
 at least one non-transitory computer-readable medium within the inner region comprising instructions to cause the at least one processor to:
  (i) determine a parameter associated with sleep of an individual based on the received backscattered RF signals; and (ii) prescribe an action that, when carried out, modifies an environmental condition that, when changed, modifies the parameter, resulting in an improvement of the sleep of the individual; and
a natural convection spatial flow path flowing from the inner region and through at least one of the plurality of openings to the exterior region to draw heat from the at least one processor and the RF components without use of a fan, thereby avoiding fan-produced noise and vibration.

11. The apparatus of example 10, further comprising a heat sink having a plurality of fins, the heat sink coupled to the at least one processor and the RF components and wherein the natural convection spatial flow path flows along and between adjacent fins.

12. The apparatus of any of the preceding examples, wherein the at least one processor includes a processor optimized for artificial intelligence algorithms.

13. The apparatus of any of the preceding examples, further comprising a speaker located beneath the at least one processor and the RF components.

14. The apparatus of any of the preceding examples, wherein the parameter associated with the sleep is determined based on a change in the backscattered signal.

15. The apparatus of any of the preceding examples, wherein the change in the backscattered signal is caused by a vibration of at least a portion of a body of the individual and thereby the backscattered signal indicates that the vibration has occurred.

16. The apparatus of any of the preceding examples, wherein the parameter associated with the sleep comprises a vital sign that is determined based at least in part on the vibration.

17. The apparatus of any of the preceding examples, further comprising a microphone that receives an audio signal from the individual or from an environment in which the individual is sleeping.

18. The apparatus of claim 17, wherein the instructions further cause the at least one processor to associate the audio signal with a factor that affects the sleep of the individual.

19. A method performed by an apparatus for sleep monitoring, the apparatus comprising:
a housing having an inner region and an exterior region enclosing the inner region;
a plurality of openings configured on the exterior region and fluidly coupled with the inner region;
radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
at least one processor within the inner region;
a natural convection spatial flow path flowing from the inner region and through at least one of the plurality of openings to the exterior region to draw heat from the at least one processor and the RF components without use of a fan, thereby avoiding fan-produced noise and vibration; and
at least one non-transitory computer-readable medium within the inner region comprising instructions to perform the method, the method comprising:

(i) determine a parameter associated with sleep of an individual based on the received backscattered RF signals; and
(ii) prescribe an action that, when carried out, modifies the parameter, resulting in an improvement of the sleep of the individual.

20. An apparatus for monitoring activities of daily life, comprising:
a housing having an inner region and an exterior region enclosing the inner region;
a plurality of openings configured on the exterior region and that communicate with the inner region;
radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
at least one processor within the inner region;
at least one non-transitory computer-readable medium within the inner region comprising instructions to cause the at least one processor to:
(i) determine a parameter associated with an activity of daily life of an individual based on the received backscattered RF signals; and
(ii) prescribe an action that, when carried out, modifies the parameter, resulting in an improvement of the activity of daily life; and
a natural convection spatial flow path flowing from the inner region and through at least one of the plurality of openings to the exterior region to draw heat from the at least one processor and the RF components without use of a fan, thereby avoiding fan-produced noise and vibration.

The specification and drawings are, accordingly, to be regarded in an illustrative rather than a restrictive sense. It will, however, be evident that various modifications and changes may be made thereunto without departing from the broader spirit and scope of the embodiments of the invention as set forth in the claims.

What is claimed is:

1. An apparatus for sleep monitoring, comprising:
a housing having an inner region and an exterior region enclosing the inner region;
a plurality of openings configured on the exterior region and that communicate with the inner region;
radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
at least one processor within the inner region;
at least one non-transitory computer-readable medium within the inner region comprising instructions to cause the at least one processor to:
(i) determine a parameter associated with sleep of an individual based on the received backscattered RF signals; and
(ii) prescribe an action that, when carried out, modifies the parameter, resulting in an improvement of sleep of the individual; and
a natural convection spatial flow path flowing from the inner region and through at least one of the plurality of openings to the exterior region to draw heat from the at least one processor and the RF components without use of a fan, thereby avoiding fan-produced noise and vibration.

2. The apparatus of claim 1, further comprising a heat sink having a plurality of fins, the heat sink coupled to the at least one processor and the RF components and wherein the natural convection spatial flow path flows along and between adjacent fins.

3. The apparatus of claim 1, wherein the at least one processor includes a processor optimized for artificial intelligence algorithms.

4. The apparatus of claim 1, further comprising a speaker located beneath the at least one processor and the RF components.

5. The apparatus of claim 1, wherein the parameter associated with the sleep is determined based on a change in the backscattered signal.

6. The apparatus of claim 5, wherein the change in the backscattered signal is caused by a vibration of at least a portion of a body of the individual and thereby the backscattered signal indicates that the vibration has occurred.

7. The apparatus of claim 6, wherein the parameter associated with the sleep comprises a vital sign that is determined based at least in part on the vibration.

8. The apparatus of claim 1, further comprising a microphone that receives an audio signal from the individual or from an environment in which the individual is sleeping.

9. The apparatus of claim 8, wherein the instructions further cause the at least one processor to associate the audio signal with a factor that affects the sleep of the individual.

10. An apparatus for sleep monitoring, comprising:
a housing having an inner region and an exterior region enclosing the inner region;
a plurality of openings configured on the exterior region and fluidly coupled to the inner region;
radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
at least one processor within the inner region;
at least one non-transitory computer-readable medium within the inner region comprising instructions to cause the at least one processor to:
(i) determine a parameter associated with sleep of an individual based on the received backscattered RF signals; and
(ii) prescribe an action that, when carried out, modifies an environmental condition that, when changed, modifies the parameter, resulting in an improvement of the sleep of the individual; and
a natural convection spatial flow path flowing from the inner region and through at least one of the plurality of openings to the exterior region to draw heat from the at least one processor and the RF components without use of a fan, thereby avoiding fan-produced noise and vibration.

11. The apparatus of claim 10, further comprising a heat sink having a plurality of fins, the heat sink coupled to the at least one processor and the RF components and wherein the natural convection spatial flow path flows along and between adjacent fins.

12. The apparatus of claim 10, wherein the at least one processor includes a processor optimized for artificial intelligence algorithms.

13. The apparatus of claim 10, further comprising a speaker located beneath the at least one processor and the RF components.

14. The apparatus of claim 10, wherein the parameter associated with the sleep is determined based on a change in the backscattered signal.

15. The apparatus of claim 14, wherein the change in the backscattered signal is caused by a vibration of at least a portion of a body of the individual and thereby the backscattered signal indicates that the vibration has occurred.

16. The apparatus of claim 15, wherein the parameter associated with the sleep comprises a vital sign that is determined based at least in part on the vibration.

17. The apparatus of claim 10, further comprising a microphone that receives an audio signal from the individual or from an environment in which the individual is sleeping.

18. The apparatus of claim 17, wherein the instructions further cause the at least one processor to associate the audio signal with a factor that affects the sleep of the individual.

19. A method performed by an apparatus for sleep monitoring, the apparatus comprising:
a housing having an inner region and an exterior region enclosing the inner region;
a plurality of openings configured on the exterior region and fluidly coupled with the inner region;
radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
at least one processor within the inner region;
a natural convection spatial flow path flowing from the inner region and through at least one of the plurality of openings to the exterior region to draw heat from the at least one processor and the RF components without use of a fan, thereby avoiding fan-produced noise and vibration; and
at least one non-transitory computer-readable medium within the inner region comprising instructions to perform the method, the method comprising:
(i) determine a parameter associated with sleep of an individual based on the received backscattered RF signals; and
(ii) prescribe an action that, when carried out, modifies the parameter, resulting in an improvement of the sleep of the individual.

20. An apparatus for monitoring activities of daily life, comprising:
a housing having an inner region and an exterior region enclosing the inner region;
a plurality of openings configured on the exterior region and that communicate with the inner region;
radio frequency (RF) components including an RF transmit antenna coupled to an RF generator and an RF receive antenna coupled to an RF receiver, the RF transmit antenna configured to emit RF signals and the receive antenna configured to receive backscattered RF signals derived from the emitted RF signals, the RF components being disposed within the inner region;
at least one processor within the inner region;
at least one non-transitory computer-readable medium within the inner region comprising instructions to cause the at least one processor to:

(i) determine a parameter associated with an activity of daily life of an individual based on the received backscattered RF signals; and
(ii) prescribe an action that, when carried out, modifies the parameter, resulting in an improvement of the activity of daily life; and
a natural convection spatial flow path flowing from the inner region and through at least one of the plurality of openings to the exterior region to draw heat from the at least one processor and the RF components without use of a fan, thereby avoiding fan-produced noise and vibration.

\* \* \* \* \*